US006497645B1

United States Patent
Halpern

(10) Patent No.: US 6,497,645 B1
(45) Date of Patent: Dec. 24, 2002

(54) REMOTE AFTERLOADER

(75) Inventor: David Halpern, Alpharetta, GA (US)

(73) Assignee: Isotron, Inc., Alpharetta, GA (US)

( * ) Notice: Subject to any disclaimer, the term of this patent is extended or adjusted under 35 U.S.C. 154(b) by 0 days.

(21) Appl. No.: 09/649,236

(22) Filed: Aug. 28, 2000

(51) Int. Cl.$^7$ ................................................ A61N 5/00
(52) U.S. Cl. ................................................ 600/3
(58) Field of Search ........................................ 600/1–8

(56) References Cited

U.S. PATENT DOCUMENTS

| 4,112,306 A | 9/1978 | Nunan | 250/499 |
| 4,150,298 A | 4/1979 | Brault et al. | 250/497 |

(List continued on next page.)

OTHER PUBLICATIONS

Rolf. F. Barth, et al., "Boron Neutron Capture Therapy for Cancer", Scientific American, Oct. 1990, pp. 100–107.

R. C. Martin et al., "Development of High-activity $^{252}$Cf Sources for Neutron Brachytherapy", Appl. Radiat. Isot., vol. 48, pp. 1567–1570, 1997.

(List continued on next page.)

*Primary Examiner*—Kevin Shaver
*Assistant Examiner*—Joseph A. Cadugan
(74) *Attorney, Agent, or Firm*—Gray Cary Ware & Friedenrich LLP

(57) ABSTRACT

The present invention provides a remote afterloader for moving a radiation source into and out of a catheter inserted in a tumor may include one or more radiation source cassettes, one or more motors, and a shielded container for storing the radiation source cassettes and the motor. Each radiation source cassette may include a radiation source wire having the radiation source connected to a treating end and a dummy source wire having a dummy source connected to a treating end. The motor advances and retracts the radiation source wire and the dummy source wire into and out of each radiation source cassette one at a time.

71 Claims, 21 Drawing Sheets

U.S. PATENT DOCUMENTS

| | | | |
|---|---|---|---|
| 4,197,170 A | | 4/1980 | Malson et al. ............... 204/1.5 |
| 4,508,119 A | | 4/1985 | Tukamoto ............... 128/329 A |
| 4,510,924 A | | 4/1985 | Gray .......................... 128/1.2 |
| 4,631,415 A | * | 12/1986 | Sauerwein et al. ......... 600/1 X |
| 4,760,266 A | | 7/1988 | Schulz ..................... 250/493.1 |
| 4,763,642 A | | 8/1988 | Horowitz ..................... 128/1.2 |
| 4,819,618 A | | 4/1989 | Liprie ............................ 600/7 |
| 4,851,694 A | | 7/1989 | Rague et al. ............. 250/497.1 |
| 4,853,550 A | | 8/1989 | Schulz ..................... 250/493.1 |
| H669 H | | 9/1989 | Fairchild et al. ............... 600/3 |
| 4,891,165 A | | 1/1990 | Suthanthrian ............... 252/633 |
| 4,897,076 A | | 1/1990 | Puthawala et al. ............. 600/7 |
| 4,957,476 A | | 9/1990 | Cano ............................. 600/7 |
| 4,963,128 A | | 10/1990 | Daniel et al. .................. 600/7 |
| 4,994,013 A | | 2/1991 | Suthanthiran et al. ......... 600/8 |
| 5,084,002 A | | 1/1992 | Liprie ............................ 600/7 |
| 5,092,834 A | * | 3/1992 | Bradshaw et al. ............. 600/7 |
| 5,103,395 A | * | 4/1992 | Spako et al. ................ 600/3 X |
| 5,139,473 A | | 8/1992 | Bradshaw et al. ............. 600/3 |
| 5,141,487 A | | 8/1992 | Liprie ............................ 600/7 |
| 5,183,455 A | | 2/1993 | Hayman et al. ............... 600/7 |
| 5,199,939 A | | 4/1993 | Dake et al. ..................... 600/3 |
| 5,267,960 A | | 12/1993 | Hayman et al. ............. 604/106 |
| 5,282,781 A | | 2/1994 | Liprie ............................ 600/3 |
| 5,317,616 A | | 5/1994 | Swerdloff et al. ............. 378/65 |
| 5,322,499 A | | 6/1994 | Liprie ............................ 600/8 |
| 5,342,283 A | | 8/1994 | Good ............................. 600/8 |
| 5,364,336 A | | 11/1994 | Carr ............................... 600/2 |
| 5,395,300 A | | 3/1995 | Liprie ............................ 600/3 |
| 5,429,582 A | | 7/1995 | Williams ....................... 600/2 |
| 5,498,227 A | | 3/1996 | Mawad .......................... 600/3 |
| 5,503,614 A | | 4/1996 | Liprie ............................ 600/7 |
| 5,531,662 A | | 7/1996 | Carr ............................... 600/2 |
| 5,562,594 A | | 10/1996 | Weeks ........................... 600/3 |
| 5,575,749 A | | 11/1996 | Liprie ............................ 600/3 |
| 5,599,796 A | | 2/1997 | Schinazi et al. ............... 514/44 |
| 5,616,114 A | | 4/1997 | Thornton et al. .............. 600/3 |
| 5,618,266 A | | 4/1997 | Liprie .......................... 604/21 |
| 5,624,372 A | | 4/1997 | Liprie ............................ 600/3 |
| 5,643,171 A | | 7/1997 | Bradshaw et al. ............. 600/1 |
| 5,662,580 A | | 9/1997 | Bradshaw et al. ............. 600/3 |
| 5,713,828 A | | 2/1998 | Coniglione .................... 600/7 |
| 5,720,717 A | | 2/1998 | D'Andrea .................... 604/21 |
| 5,722,985 A | | 3/1998 | Pettus ........................ 606/180 |
| 5,782,741 A | | 7/1998 | Bradshaw et al. ............. 600/3 |
| 5,788,713 A | | 8/1998 | Dubach et al. ............. 606/130 |
| 5,800,333 A | | 9/1998 | Liprie ............................ 600/3 |
| 5,803,895 A | | 9/1998 | Kronholz et al. .............. 600/3 |
| 5,807,231 A | | 9/1998 | Liprie ............................ 600/3 |
| 5,833,593 A | | 11/1998 | Liprie ............................ 600/3 |
| 5,840,008 A | | 11/1998 | Klein et al. .................... 600/3 |
| 5,851,172 A | * | 12/1998 | Bueche et al. ................. 600/7 |
| 5,857,956 A | | 1/1999 | Liprie ............................ 600/7 |
| 5,860,909 A | | 1/1999 | Mich et al. ..................... 600/7 |
| 5,863,284 A | | 1/1999 | Klein ............................. 600/3 |
| 5,866,127 A | | 2/1999 | Senger et al. ............. 424/178.1 |
| 5,868,757 A | | 2/1999 | Koutrouvelis ............... 606/130 |
| 5,872,107 A | | 2/1999 | Schinazi et al. ............... 514/44 |
| 5,882,291 A | | 3/1999 | Bradshaw et al. ............. 600/3 |
| 6,048,300 A | * | 4/2000 | Thornton et al. .............. 600/7 |
| 6,095,975 A | * | 8/2000 | Silvern ...................... 600/3 X |
| 6,196,963 B1 | * | 3/2001 | Williams ....................... 600/3 |
| 6,283,911 B1 | * | 9/2001 | Keren ............................ 600/3 |

OTHER PUBLICATIONS

Yosh Maruyama, M.D., FACR, et al., "Californium–252 Neutron Brachytherapy", From Nag S (ed): Principles and Practice of Brachytherapy, pp. 649–687, 1997.

R.A. Patchell, M.D., et al., "A phase I trial of neturon brachytherapy for the treatment of malignant gliomas", The British Journal of Radiology, 70, pp. 1162–1168, 1997.

Yosh Maruyama, M.D., FACR, et al., "Study of Biological Effects of Varying Mixtures of Cf–252 and Gamma Radiation on the Acute Radiation Syndromes: Relevance to Clinical Radiotherapy of Radioresistant Cancer", I. J. Radiation Oncology, Biology, Physics, vol. 27, No. 4, pp. 907–914, 1993.

J.C. Yanch, et al., "Dosimetry of $^{252}$Cf Sources for Neutron Radiotherapy with and without Augmentation by Boron Neutron Capture Therapy", Radiation Research, 131, pp. 249–256, 1992.

Roy A. Patchell, M.D., et al., "Postoperative Radiotherapy in the Treatment of Single Metastases to the Brain," JAMA, vol. 280, No. 17, pp. 1485–1489, Nov. 1998.

Jeffrey A. Coderr, et al., Review, "The Radiation Biology of Boron Neutron Capture Therapy", Radiation Research, 151, pp. 1–18, 1999.

Darrel D. Joel, et al., "Effect of dose and infusion time on the delivery of p–boronophenylalanine for neutron capture therapy", Journal of Neuro–Oncology 41, pp. 213–221, 1999.

J.G. Wierzbicki, et al., Measurement of augmentation of $^{252}$Cf implant by $^{10}$B and $^{157}$Gd neutron capture, Med. Phys., 21 (6), pp. 787–790, Jun. 1994.

Patrick J. Kelly, M.D., "Computer–Directed Stereotactic Resection of Brain Tumors", Neurosurgical Operative Atlas, vol. 1 (4), pp. 299–313, 1991.

Setti S. Rengachary, M.D., "Frontal Lobectomy", Neurosurgical Operative Atllas, vol. 3, pp. 175–183, 1993.

Raymond D. Adams, M.A., M.D., et al., "The Major Categories of Neurologic Disease", Principles of Neurology, Part IV, CH. 30, pp. 446–455, 1981.

Jeffrey D. MacDonald, M.D. Ph.D., et al., "Interstitial Brachytherapy", Neurosurgical Operative Atlas, vol. 2(2), pp. 143–151, 1992.

Maruyama: "Work in Progress: $^{252}$CF Neutron Brachytherapy for Hemispheric Malignant Glioma[1]" Radiology. Oct. 1982. vol. 145. No. 1. pp. 171–174.

Barthelemy, P. et al. "The Development of Californium–252 Sealed Sources at the Commissariat A L'Energie Atomique" Nuclear Technology. Jun. 1975. vol. 26. No. 2. pp. 201–214.

Zeng, S. X. et al. "Cf–252 Neutron Theraphy in China" R&D Division, Cafmed, Beijing 100036, PRC.

Maruyama, Y. "Progress Report $^{252}$Cf Radiation Oncology Study and Evaluation Project" University of Kentucky Medical Center, 1991.

* cited by examiner

REMOTE AFTERLOADER

TECHNICAL FIELD OF THE INVENTION

The present invention relates generally to the field of radiotherapy. In particular, this invention relates to a remote controlled, automated delivery system used to advance, retract, and store isotopic neutron sources for treating cancer tumors and the like.

BACKGROUND OF THE INVENTION

Various diseases and disorders can cause undesirable cells to grow within the body of a patient. The most insidious of these diseases is cancer. Cancer is a condition where undesirable cells multiply uncontrollably forming cancerous tumors in the patient's body. To effectively treat cancer, surgery is generally required to remove as many of the cancer cells as possible. After surgery, various treatment methods such as chemotherapy and/or radiation treatment are used to damage or kill the remaining undesirable cells in the patient's body.

Some forms of cancer, such as cancerous brain tumors, are inoperable, and chemotherapy or conventional radiation treatment alone are not sufficient to combat and destroy the cancerous tumor cells. External radiation treatments are typically given to patients, however, as the depth for any one of the various tumors increases, the surrounding area gets exposed to more radiation. To overcome this obstacle, another treatment called brachytherapy was developed. Brachytherapy treatment is a method in which a radiation source is inserted into or near the cancerous tumor, thus the radiation is more focused toward the cancerous tumor cells and less damage occurs to surrounding healthy cells. Radiation sources used in brachytherapy may include various elements which emit various types of radiation or particles, including beta particles and gamma photons. Gamma photons and beta particles are referred to as low linear-energy-transfer (LET) radiation particles in which a particle transfers a small amount of its energy to a tumor cell on each passage. To effectively kill the cancerous tumor cells, the small amount of energy transferred to each cancerous tumor cell must be converted into free radicals via interaction with the oxygen existing within the cancerous tumor cells. Thus, low LET radiation treatment is ineffective against cancer cells which are hypoxic (have less oxygen than typical healthy cells). Hypoxic cells are found in cancerous tumors, such as brain tumors, melanoma, and sarcoma, that are more filly developed (Stage III or Stage IV).

High LET radiation sources, such as neutrons, may be more effective for treating hypoxic cancerous tumor cells (see R. A. Patchell et al., "A phase I trial of neutron brachytherapy for the treatment of malignant gliomas", *The British Journal of Radiology*, Vol. 70, pp. 1162–1168 (November 1997)). Examples of neutron sources can be a radioactive element, such as californium (Cf-252), that may be internally placed near the tumor cells (i.e. the brachytherapy source) or an external neutron beam produced by a nuclear reactor or proton /deuteron accelerator. These neutron sources emit neutrons which collide with the hydrogen nuclei of the cancerous tumor cells. The recoil hydrogen nuclei (i.e. protons) then break chemical bonds of the essential molecules (e.g. DNA) in the cancerous tumor cells and cause the cells to be damaged and die. The interaction of the high LET radiation sources with the cancerous tumor cells is not dependant on the amount of oxygen that is present in each of the cancerous tumor cells, but rather hydrogen. Both oxic and hypoxic cells contain hydrogen. Thus a neutron treatment is equally effective at killing or damaging both normal cancerous tumor cells and hypoxic cancerous tumor cells.

A delivery system known as an afterloader is used to advance, retract and store highly concentrated isotopic sources used in brachytherapy treatment. Typical afterloaders delivering beta and gamma sources are relatively small (weighing 300 lbs), designed as a standalone piece of equipment, and are generally stationed in the same room as the patient, adjacent to the patient's bedside. To administer a brachytherapy treatment, healthcare workers typically place multiple catheters and/or needles into the patient's tumor and connect them to the afterloader before leaving the patient's room. After running a start-up routine and program, current afterloaders deliver a non-active (dummy) source into the first catheter to verify proper placement. If successful, the dummy source wire is retracted and an active source wire is delivered into the catheter. Next, the afterloader advances to the next catheter/needle location and delivers a dummy source followed by the active source. This procedure continues until all of the catheter/needle locations have successfully been radiated.

Radiation treatments with neutron sources using Cf-252 have various limitations. One problem is that the sources are large in size and the intensity of radioactive material is low. Handling and deploying of such sources is done manually. The types of cancerous tumors treated in this matter have been mainly intracavity tumors, such as cervical and head and neck tumors with some success. However, interstitial treatment of high grade brain tumors was also undertaken. Unfortunately, because of the long irradiation time (~30 hours) and the lack of precision in dose delivery caused the patients to suffer from infection and necrosis.

SUMMARY OF THE INVENTION

The present invention provides a remote afterloader suitable for use in brachytherapy with small, high intensity neutron sources.

The present invention provides a remote afterloader for simultaneously delivering and positioning multiple radiation sources in cancerous tumors. The remote afterloader for moving a radiation source into and out of a catheter inserted in a tumor may include one or more radiation source cassettes, one or more motors, and a shielded container for storing the radiation source cassettes and the motor. Each radiation source cassette may include a radiation source wire having the radiation source connected to a treating end and a dummy source wire having a dummy source connected to a treating end. The motor advances and retracts the radiation source wire and the dummy source wire into and out of each radiation source cassette one at a time.

The present invention also provides a radiation source cassette for storing a radiation source. The radiation source cassette may include a radiation source wire having the radiation source connected to a treating end and a dummy source wire having a dummy source connected to a treating end. Furthermore, a motor can be used to advance and retract the radiation source wire and the dummy source wire into and out of the radiation source cassette one at a time.

The present invention provides a remote afterloader having multiple motors for simultaneously delivering multiple dummy sources and neutron radiation sources through catheters or needles to multiple areas of a cancerous tumor, thus significantly reducing the patient treatment time.

The present invention also provides remote afterloader design having adequate radiation shielding and protection from high LET neutron sources such as Cf-252, thus significantly reducing the radiation exposure to the health care personnel.

The present invention also provides a remote afterloader which may serve as a long-term storage vault for radiation sources.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

Figure 1:
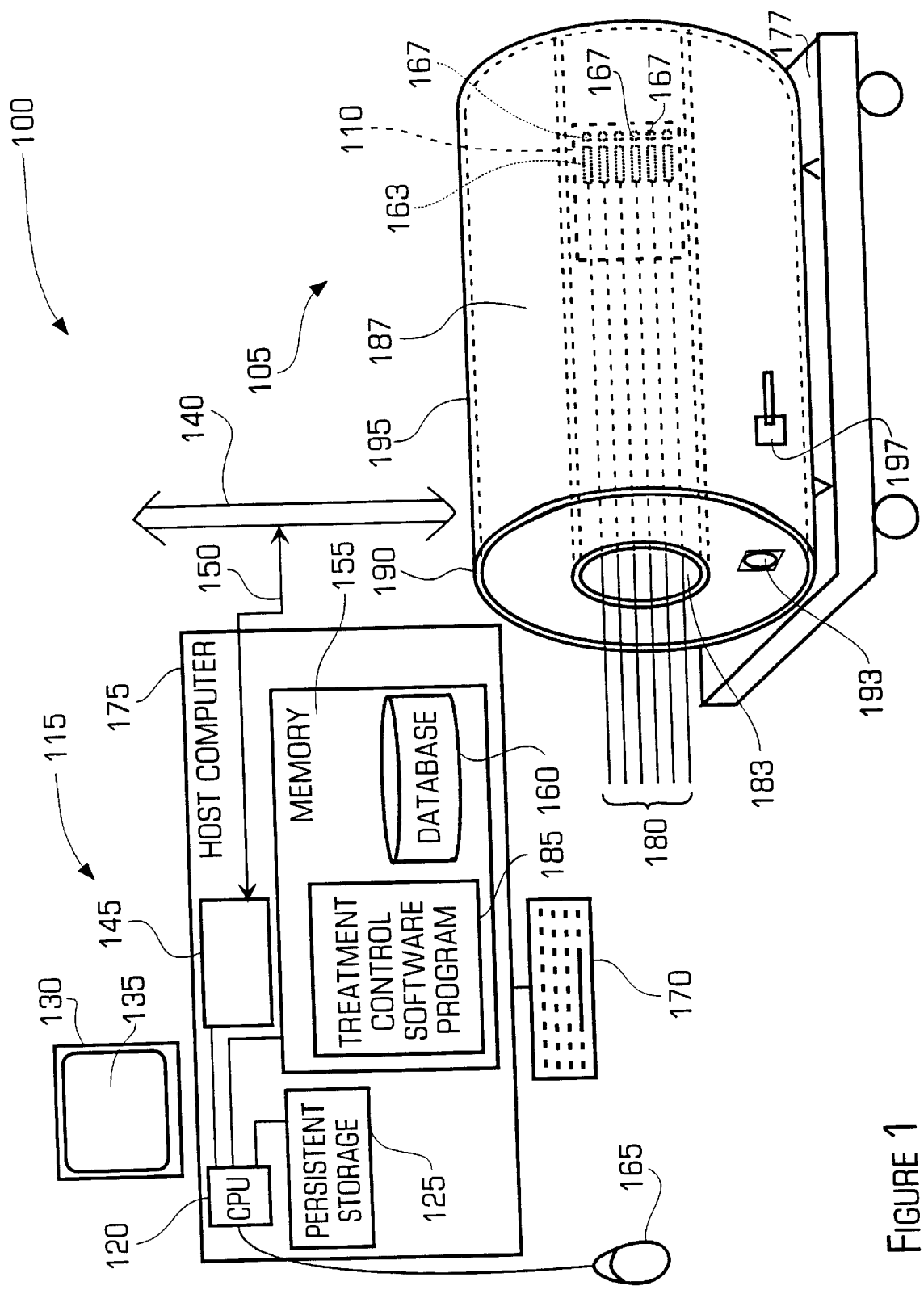
FIG. 1 shows a host computer system connected to a remote afterloader.

FIG. 1 shows one example of a remote afterloader 105 and a host system 115 for operating and controlling the afterloader 105. The remote afterloader 105 includes a storage container 195 and a radiation source cassette storage unit 110 located within the storage container 195. The radiation source cassette storage unit 110 is comprised of multiple slots for holding multiple radiation source cassettes 163. Each radiation source cassette 163 is designed to hold a radiation source wire 180 having a radioactive or neutron source attached to the end of it and a dummy source wire (FIG. 4) having a dummy source (FIG. 4) attached to the end of it. One example of a radioactive or neutron source can be californium (Cf-252). The radiation source cassette storage unit 110 also comprises multiple motors 167. Each motor 167 is connected to a particular radiation source cassette 163 to dispense or retract the radiation source wire 180. Each of the motors 167 can be independently controlled by an end user through the host system 115, thus eliminating the need for manual handling. The radiation source cassette 163 also comprises sensors (FIG. 3) which detect the presence of a catheter. An example catheter is described in co-pending US application entitled Reinforced Catheter Connector and System filed on Apr. 20, 2000, Ser. No. 09/553,743 (incorporated by reference herein in its entirety). The sensors are also electrically connected to and monitored by the host system 115.

A main switch 193 is used to turn the remote afterloader 105 on and off. The main switch 193 can be controlled both at the remote afterloader 105 and through the host system 115. The remote afterloader 105 can be powered with electricity and have a battery attached for backup power. A battery can also be used as the main power source. In the event that both the electricity and the battery fail, a manual crank 197 can be used to physically retract all the radiation sources safely back into the remote afterloader 105. The remote afterloader 105 also has several emergency stop switches connected to the remote afterloader 105, but placed in various different locations. For example, one emergency stop switch can be connected directly to the remote afterloader 105. Another emergency stop switch can be attached to a wall both inside and outside a treatment room. Yet another emergency stop switch can be activated from the host system 115.

The storage container 195 shown in FIG. 1 is cylindrical, however, the storage container 195 can be any shape. The storage container has layers of metal 190 and hydrogenous material 187 which provides radiation protection, thus eliminating the need to store the radiation sources in different storage container. The hydrogenous material 187 slows down the fast moving neutrons and the metal material 190 has a high atomic number which provides shielding against gamma rays. Examples of different hydrogenous materials 187 which can be used include wax, polyethylene, water-extended polyester resins (WEP) (such as Ashland Chemical WEP 662 P resin and hardener) and a boron additive. The water-extendible polyester resins form an emulsion with water to extend the polyester and improve physical properties. The water-extendible polyester resins can be considered water-filled foams. For a borated WEP emulsion a boron agent such as boric acid or Borax can be used. The abundant hydrogen atoms of WEP slows down fast neutrons, and the boron agent captures the slowed-down neutrons.

Examples of metal shielding materials 190 which can be used include lead, tungsten, or depleted uranium. The remote afterloader container 195 has a metal lining approximately two inches thick (lead) surrounding the cassette storage unit 110. The hydrogenous material layer 187 is approximately twelve to eighteen inches thick. Using this shielding configuration, the external radiation dose rate outside the shield is sufficiently reduced to acceptable levels for routine maintenance by medical personnel or other users. When the remote afterloader 105 is not in use, a metal layered cap can be placed over the opening 183 so that the remote afterloader 105 can serve as a storage device for the radiation source cassettes 163. The remote afterloader 105 can optionally be placed in a heavily shielded room adjacent to a treatment room for additional safety precautions to protect medical personnel or other users against over exposure of radiation. Also shown in FIG. 1 is a remote controlled platform 177 having four wheels which the remote afterloader 105 is mounted to. The remote controlled platform 177 makes it easier for a user to move the remote afterloader 105. In another embodiment, the remote controlled platform 177 can also have a fork lift type mechanism to lift, lower, and tilt the remote afterloader 105, which can be utilized during the loading process.

The host system 115 includes a host computer 175 for processing digital information. The host system 115 also includes a monitor 130 having a graphical user interface (GUI) 135 to display the digital information. The host computer 175 includes a CPU 120 for receiving and processing the digital information received by host system 115 and processed within the host computer 175. The CPU 120 is connected to persistent storage 125, such as random access memory (RAM), dynamic read only memory (DRAM), static read only memory (SRAM) and other types of memory devices, which may store one or more software applications that may be loaded into memory 155 and executed by the CPU 120. The host computer 175 is configured to control and manage a database 160 and run a treatment control software program 185. Both the database 160 and the treatment control software program 185 are stored in memory 155. The operation and features of the remote afterloader 105 together with data stored in database 160 are discussed in further detail below.

The host computer 175 may be any one of a number of general purpose computers, e.g. a personal computer (PC) configured to execute software code. The host computer 175 can be operated by a user via mouse 165 manipulating a cursor on GUI 135 (not shown) and a keyboard 170 for inputting data. The host computer 175 further includes a communications interface 145 which can connect via a communication link 150 to a network 140 for communication with the remote afterloader 105 or other computers. The communications link 150 can also be connected directly to the remote afterloader 105. The communication link 150 can include a telephone line (i.e. modem), wireless communication device, or a common network interface. The network 140 may be any one of a number of network systems including a telephone system, a cellular network system, a local area network (LAN) system, or the Internet for exchanging and transferring information.

The database 160 can be preferably configured to retain and store objects and associated documents and information and provide controlled access to information by multiple users. It can be made accessible to users on the network 140 having access privileges. The information in the database 140 may be organized by data objects that represent the information contained therein. Generally, objects encapsulate both data and methods for using the data. Object data can be of different types such as field types, which may describe a database field entry; links associating an object with other objects or documents, and other types helpful in describing or defining an object or related information. Objects may be organized into sets of objects that are related by common attributes or other affiliation. If properly defined, objects can be helpfiil in organizing and manipulating related information in a logical manner. In another embodiment, the database 160 is implemented in an object-oriented relational database, and may be distributed over the network 140. The type of information which can be stored in the database 160 include initial settings for the remote afterloader 105, specific information relating to different patients (e.g., patent's name and treatment number), and the particular speed and feed rates used for delivering and retracting the source wires 180 into and out of the patient's tumor. The host computer 175 is also configured to execute a treatment control software program 185 stored in memory 155. One function which the treatment control software program 185 performs is to independently control each motor 167 as the motor dispenses and retracts the radiation source wire into and out of a particular radiation source cassette. Other functions which the treatment control software program 185 performs are discussed in greater detail below.

Figure 2:
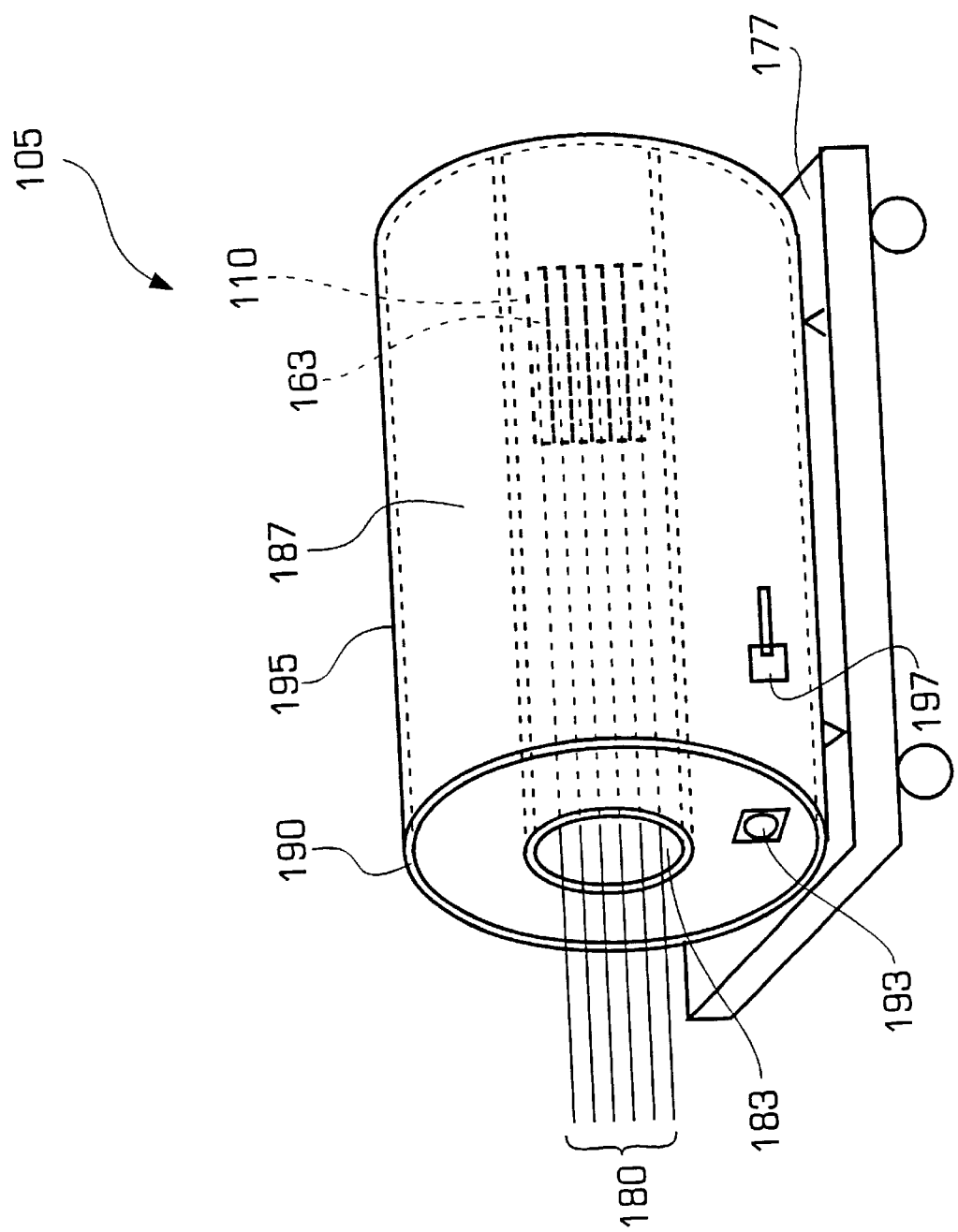
FIG. 2 shows another embodiment of the remote afterloader.
Figure 3:
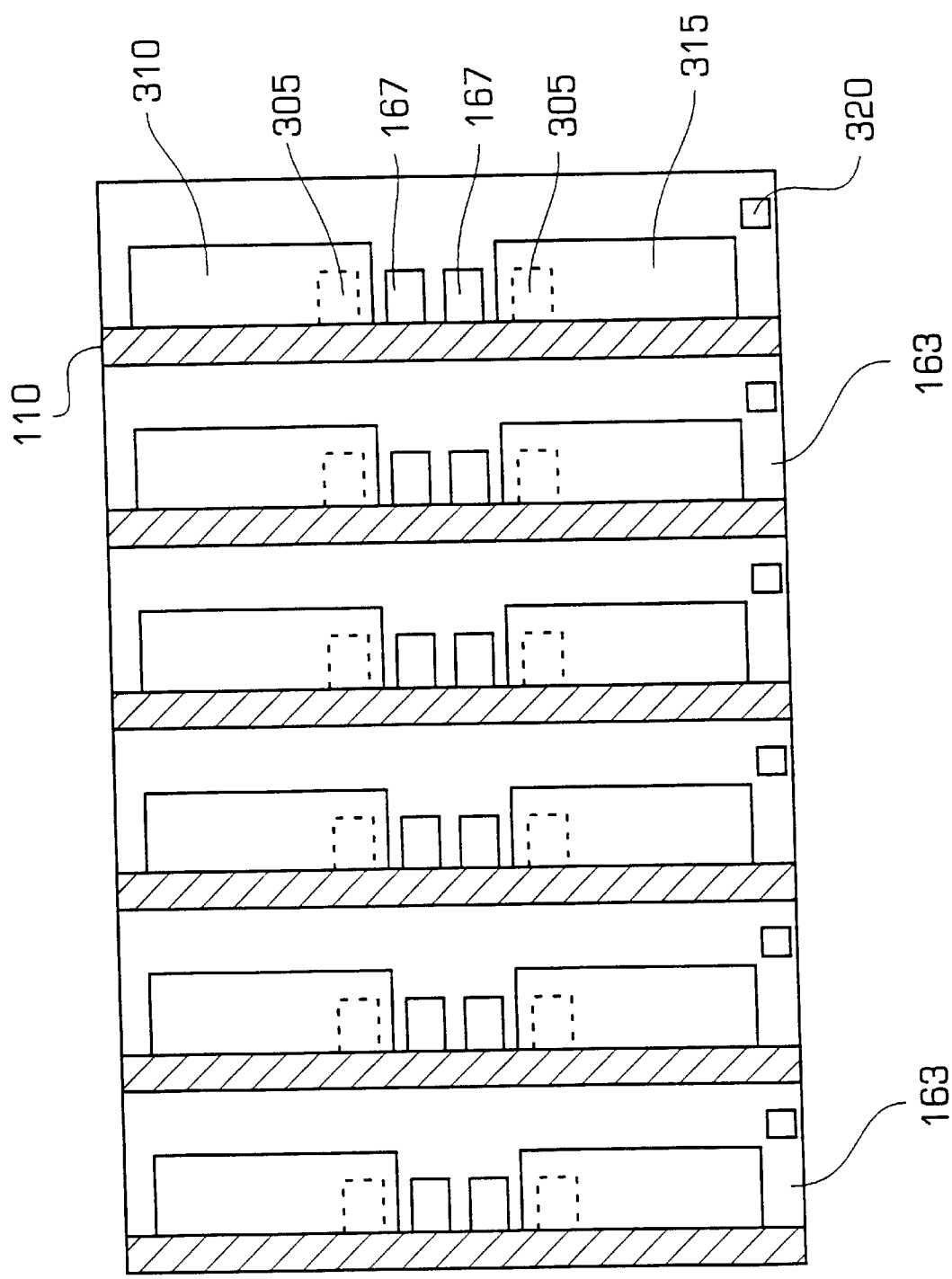
FIG. 3 shows one example of the radiation source cassette storage unit.

FIG. 2 shows another embodiment of the remote afterloader 105. This embodiment of the remote afterloader 105 also includes a storage container 195 and a radiation source cassette storage unit 110. However, the multiple motors which drive each individual radiation source cassette 163 are located within each radiation source cassette 163 instead of the radiation source cassette storage unit 110. FIG. 3 shows one example of the radiation source cassette storage unit 110 storing radiation source cassettes 163. The radiation source cassette storage unit 110 can hold multiple radiation source cassettes 163. In one embodiment, each radiation source cassette 163 includes a first reel 310, a second reel 315, one or more motors 167, one or more guide rollers 305 and a pressure sensor 320. The first reel 310 is for the active radiation source wire 180 and the second reel 315 is for the dummy source wire. Each motor 167 within each radiation source cassette 163 can be independently controlled by the host system 115.

Figure 4:
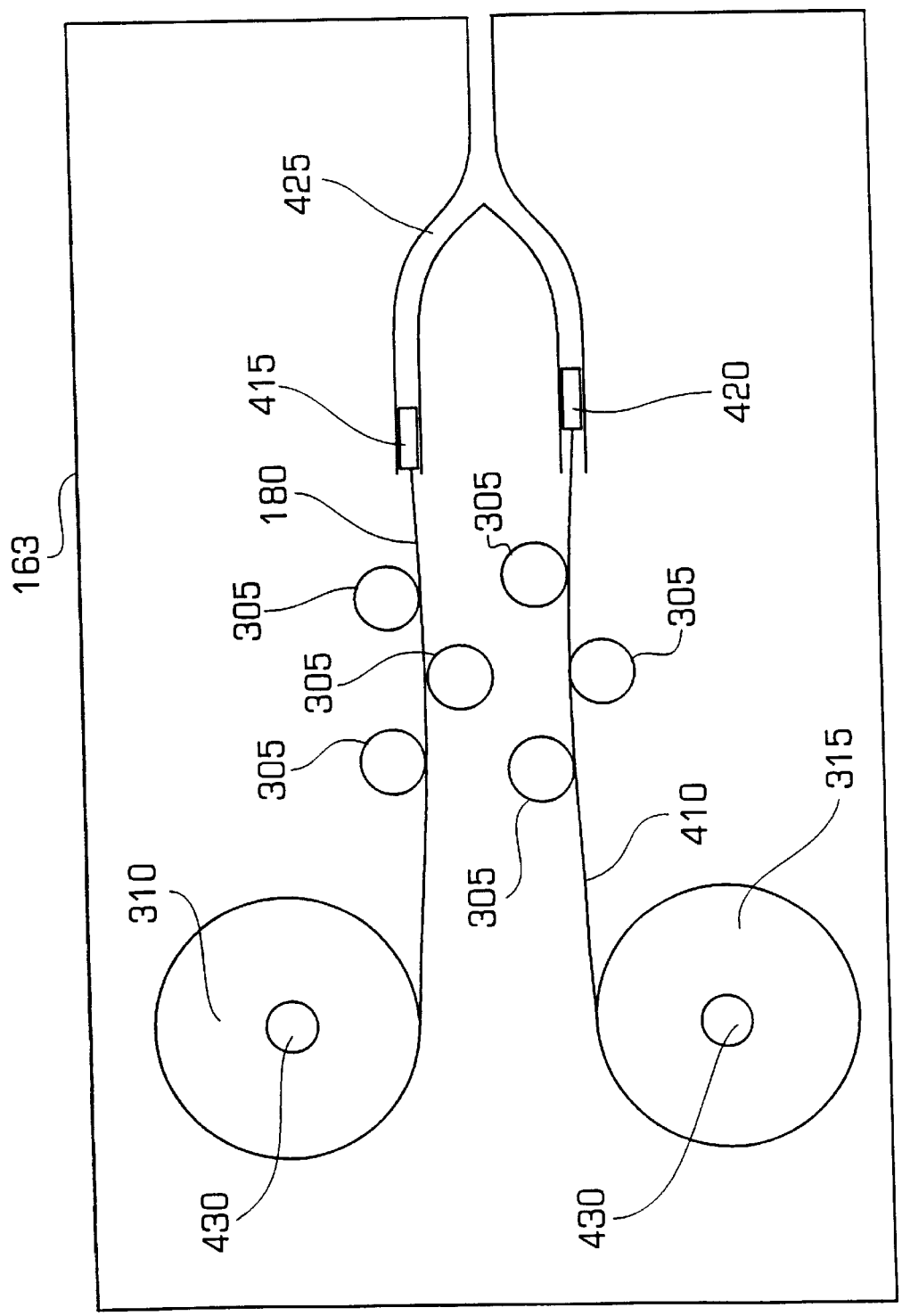
FIG. 4 shows one embodiment of a non-motorized radiation source cassette.

FIG. 4 shows one embodiment of non-motorized radiation source cassette 163. The non-motorized radiation source cassette 163 is designed to contain both a radiation source 415 attached at the end of the radiation source wire 180 and a dummy source 420 attached at the end of the dummy source wire 410. The radiation source 415 can either be active or non-active (dummy). The non-motorized radiation source cassette 163 includes a first reel 310, a second reel 315, multiple guide rollers 305, and a Y-shaped track. A bearing 430 is located at the center of both the first reel 310 and the second reel 315. The radiation source wire 180 is coiled around the first reel 310 and inserted through the guide rollers 305 so that two guide rollers 305 are located above the radiation source wire 180, and one guide roller 305 is located below the radiation source wire 180. The guide rollers 305 help to guide the radiation source 415 through the Y-shaped track as it is delivered to and retracted during radiation treatment. An example method for radiation treatment is described in co-pending U.S. application entitled Method for Treating Solid Tumors Using Neutron Therapy filed Sep. 13, 1999, Ser. No. 09/394,234 (incorporated by reference herein in its entirety). The dummy source wire 410 is coiled around the second reel 315 and inserted through the guide rollers 305 so that two guide rollers 305 are located above the dummy source wire 410, and one guide roller 305 is located below the dummy source wire 410. The guide rollers 305 help to guide the dummy source 420 through the Y-shaped track as it is delivered to and retracted from the catheters located in the patient's tumor. A non-motorized radiation source cassette 163 can work with the remote afterloader 105 described in FIG. 1 where the radiation source cassette unit includes motors for driving each cassette. The motors which are controlled by the host system 115 drive the non-motorized radiation source cassettes 163 to deliver and retract the radiation source wire 180 or the dummy source wire 410 during radiation treatment.

Figure 5:
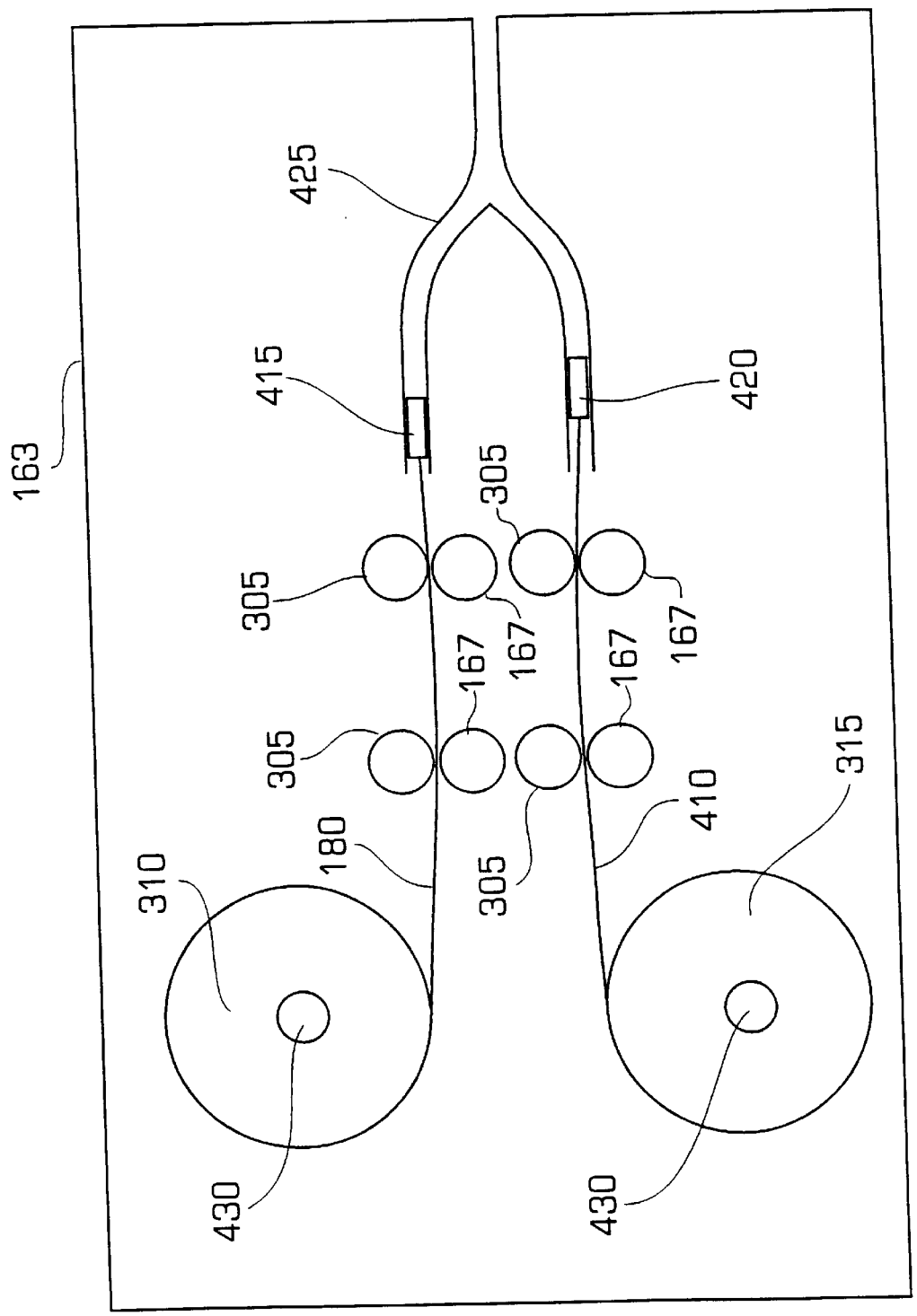
FIG. 5 shows one embodiment of a motorized radiation source cassette.

In another embodiment, the radiation source cassette 163 can be motorized. The motors 167 of a motorized radiation source cassette 163 advance or retract the radiation source wire 180 or the dummy source wire 410 into and out of the radiation source cassette 163. FIG. 5 shows one embodiment of a motorized radiation source cassette 163. The motorized radiation source cassette 163 comprises a first reel 310, a second reel, multiple motors 167, multiple guide rollers 305, and a Y-shaped track. A bearing 430 is located at the center of the first reel 310 and the second reel 315. In this embodiment, the bearing 430 can also be replaced with a motor. A bearing 430 is located at the center of both the first reel 310 and the second reel 315. The radiation source wire 180 is coiled around the first reel 310 and inserted through the guide rollers 305 and motors 167. The motors 167 drive the radiation source wire 180. The guide rollers 305 help to guide the radiation source 415 through the Y-shaped track as it is delivered to and retracted during radiation treatment. The dummy source wire 410 is coiled around the second reel 315 and inserted through the guide rollers 305 and motors 167. The guide rollers 305 help to guide the dummy source 420 through the Y-shaped track as it is delivered to and retracted from the catheters located in the patient's tumor.

Figure 6:
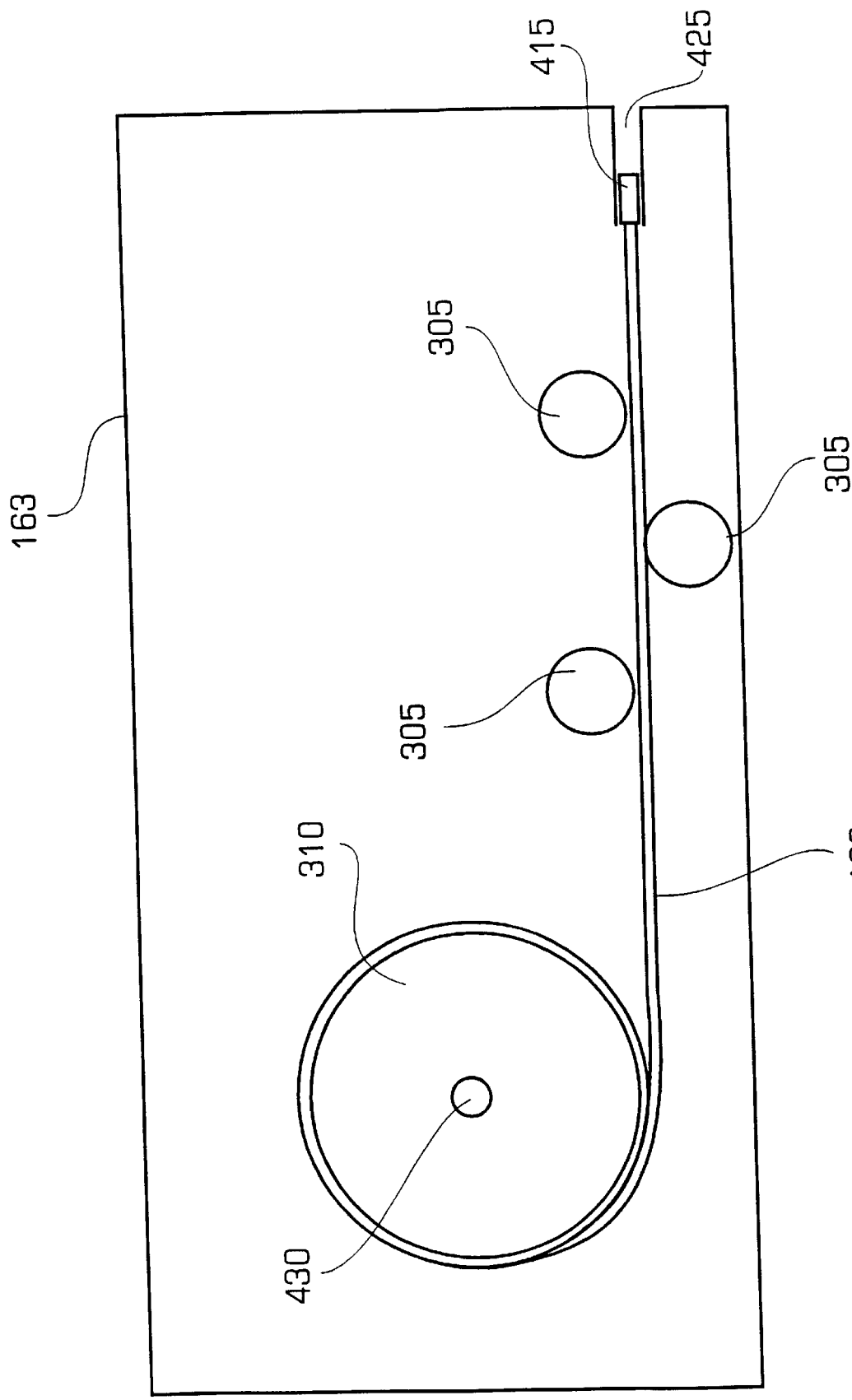
FIG. 6 shows a second embodiment of the non-motorized radiation source cassette.
Figure 7:
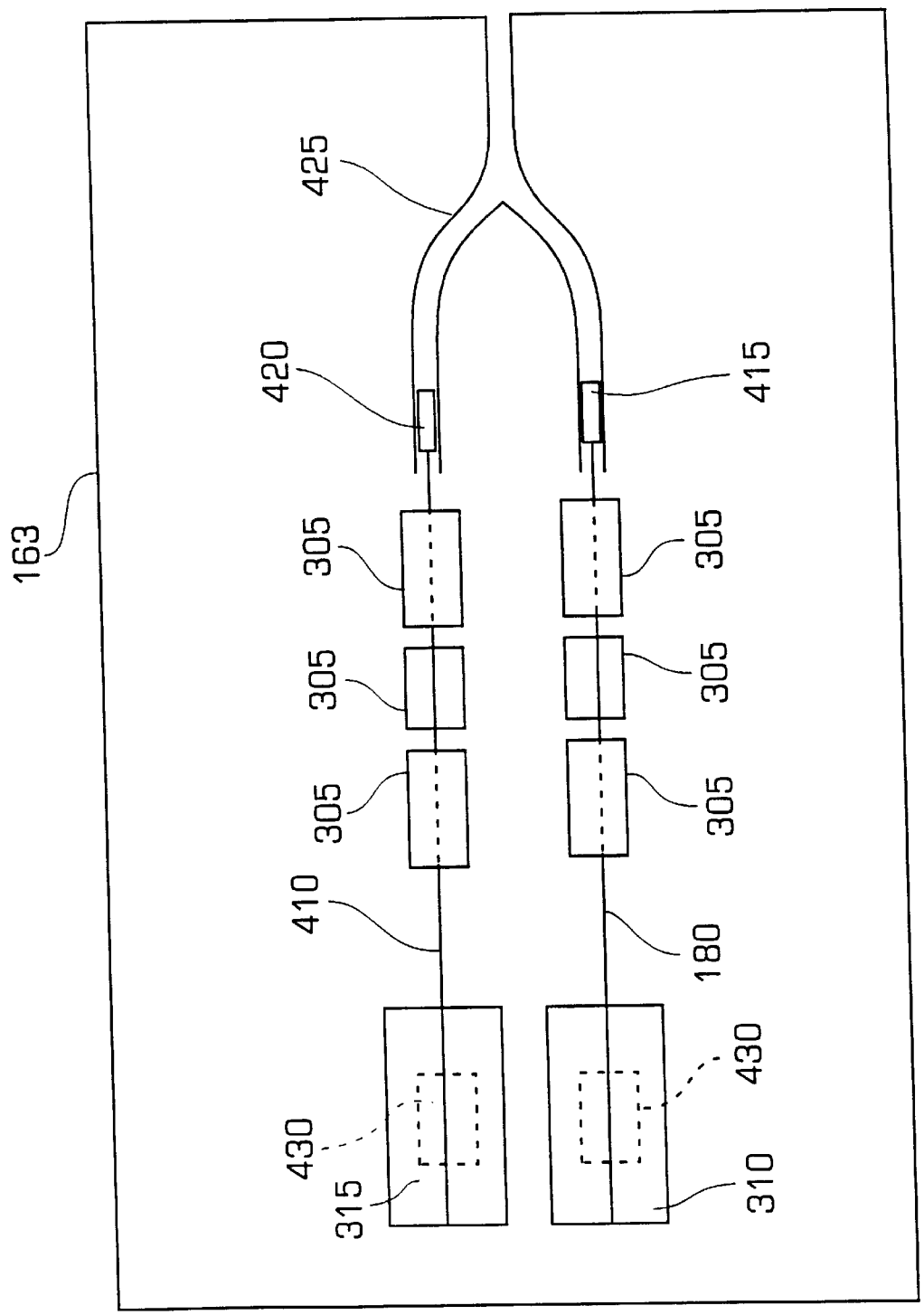
FIG. 7 shows a top view of the second embodiment of the non-motorized radiation source cassette.

FIG. 6 shows another embodiment of a non-motorized radiation source cassette 163. This embodiment of the non-motorized functions exactly the same as the non-motorized radiation source cassette shown in FIG. 4, however the layout is different. FIG. 6 shows a side view of the radiation source cassette 163. In this embodiment, the first reel 310 and the second reel 315 are located side by side as opposed to one on top of the other. FIG. 7 is a top view of this embodiment of the radiation source cassette 163 showing the first reel 310 and the second reel 315 located side by side. The non-motorized radiation source cassette 163 includes a first reel 310, a second reel 315, multiple guide rollers 305, and a Y-shaped track. A bearing 430 is located at the center of both the first reel 310 and the second reel 315. The radiation source wire 180 is coiled around the first reel 310 and inserted through the guide rollers 305 so that two guide rollers 305 are located above the radiation source wire 180, and one guide roller 305 is located below the radiation source wire 180. The guide rollers 305 help to guide the radiation source 415 through the Y-shaped track as it is delivered to and retracted during radiation treatment. The dummy source wire 410 is coiled around the second reel 315 and inserted through the guide rollers 305 so that two guide rollers 305 are located above the dummy source wire 410, and one guide roller 305 is located below the dummy source wire 410. The guide rollers 305 help to guide the dummy source 420 through the Y-shaped track as it is delivered to and retracted from the catheters located in the patient's tumor. This embodiment of the non-motorized radiation source cassette 163 can also work with the remote afterloader 105 described in FIG. 1 where the radiation source cassette unit includes motors for driving each cassette.

Figure 8:
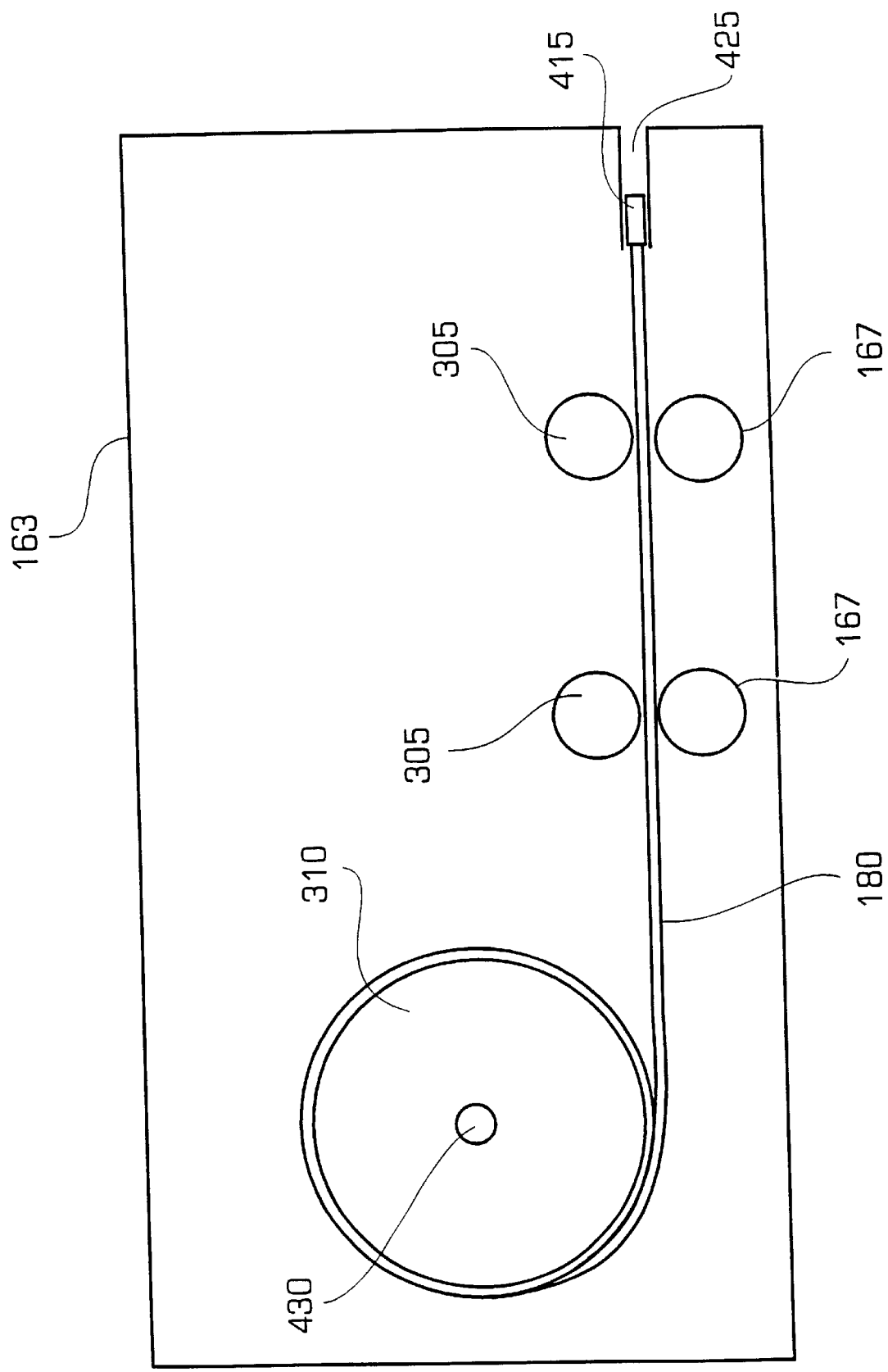
FIG. 8 shows a second embodiment of the motorized radiation source cassette.
Figure 9:
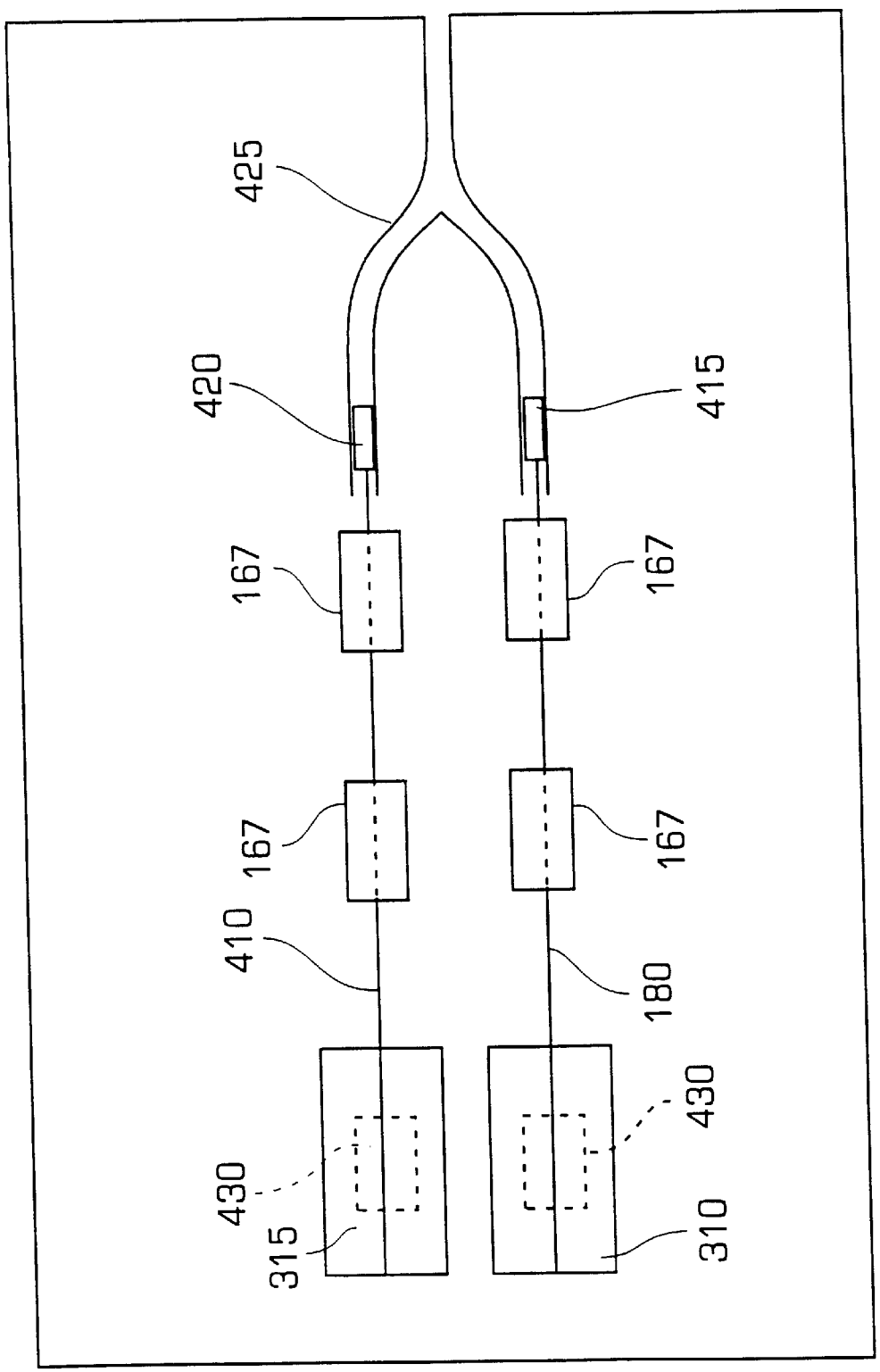
FIG. 9 shows a top view of the second embodiment of the motorized radiation source cassette.

FIG. 8 shows another embodiment of a motorized radiation source cassette 163. This embodiment of the motorized functions exactly the same as the motorized radiation source cassette shown in FIG. 5, however the layout is different. FIG. 8 shows a side view of the radiation source cassette 163. In this embodiment, the first reel 310 and the second reel 315 are located side by side as opposed to one on top of the other. FIG. 9 is a top view of this embodiment of the radiation source cassette 163 showing the first reel 310 and the second reel 315 located side by side. The motorized radiation source cassette 163 includes a first reel 310, a second reel, multiple motors 167, multiple guide rollers 305, and a Y-shaped track. A bearing 430 is located at the center of the first reel 310 and the second reel 315. In this embodiment, the bearing 430 can also be replaced with a motor. A bearing 430 is located at the center of both the first reel 310 and the second reel 315. The radiation source wire 180 is coiled around the first reel 310 and inserted through the guide rollers 305 and motors 167. The motors 167 drive the radiation source wire 180. The guide rollers 305 help to guide the radiation source 415 through the Y-shaped track as it is delivered to and retracted during radiation treatment. The dummy source wire 410 is coiled around the second reel 315 and inserted through the guide rollers 305 and motors 167. The guide rollers 305 help to guide the dummy source 420 through the Y-shaped track as it is delivered to and retracted from the catheters located in the patient's tumor.

Figure 10:
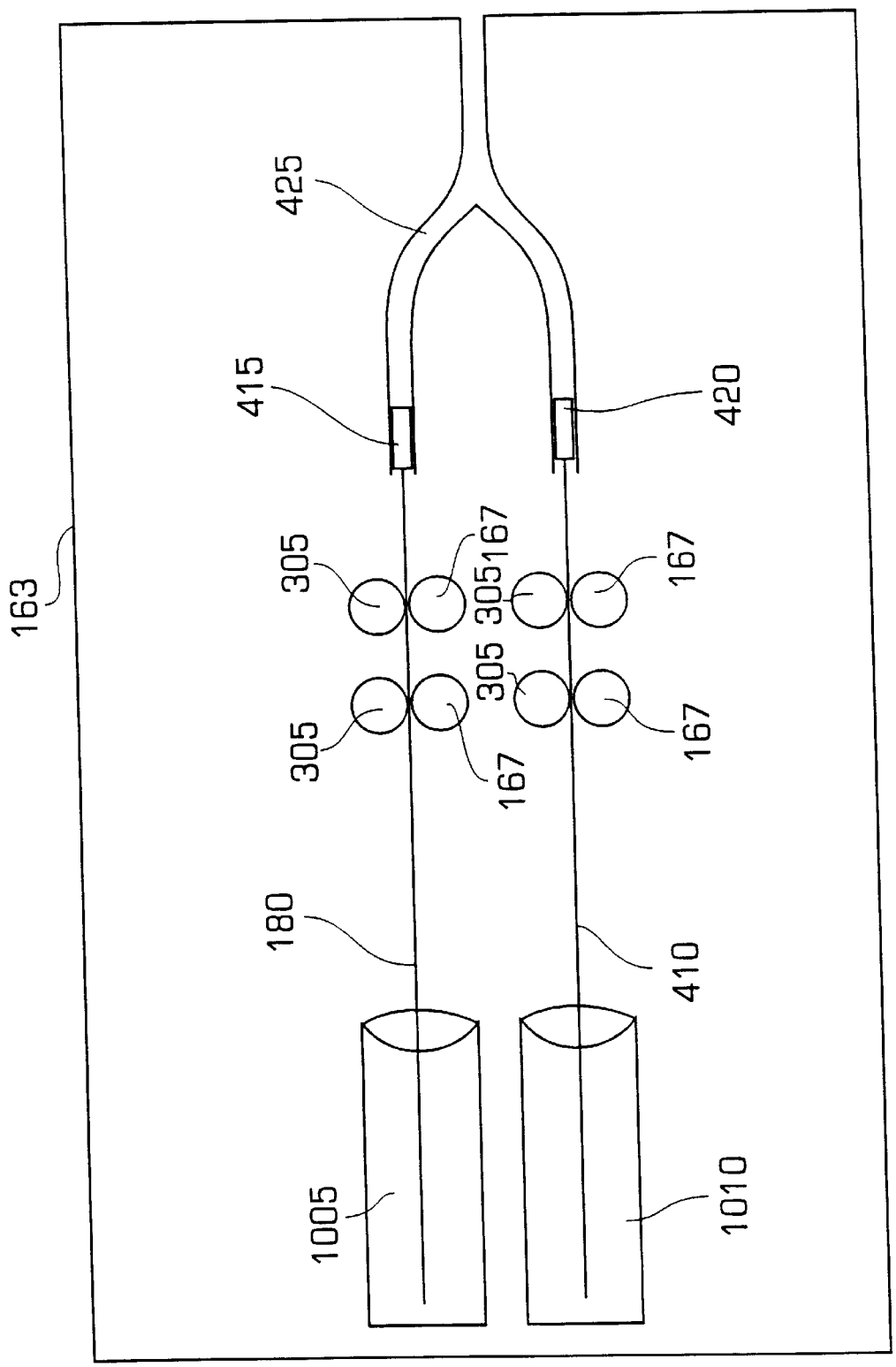
FIG. 10 shows one embodiment of the motorized radiation source cassette comprising tubes.
Figure 11:
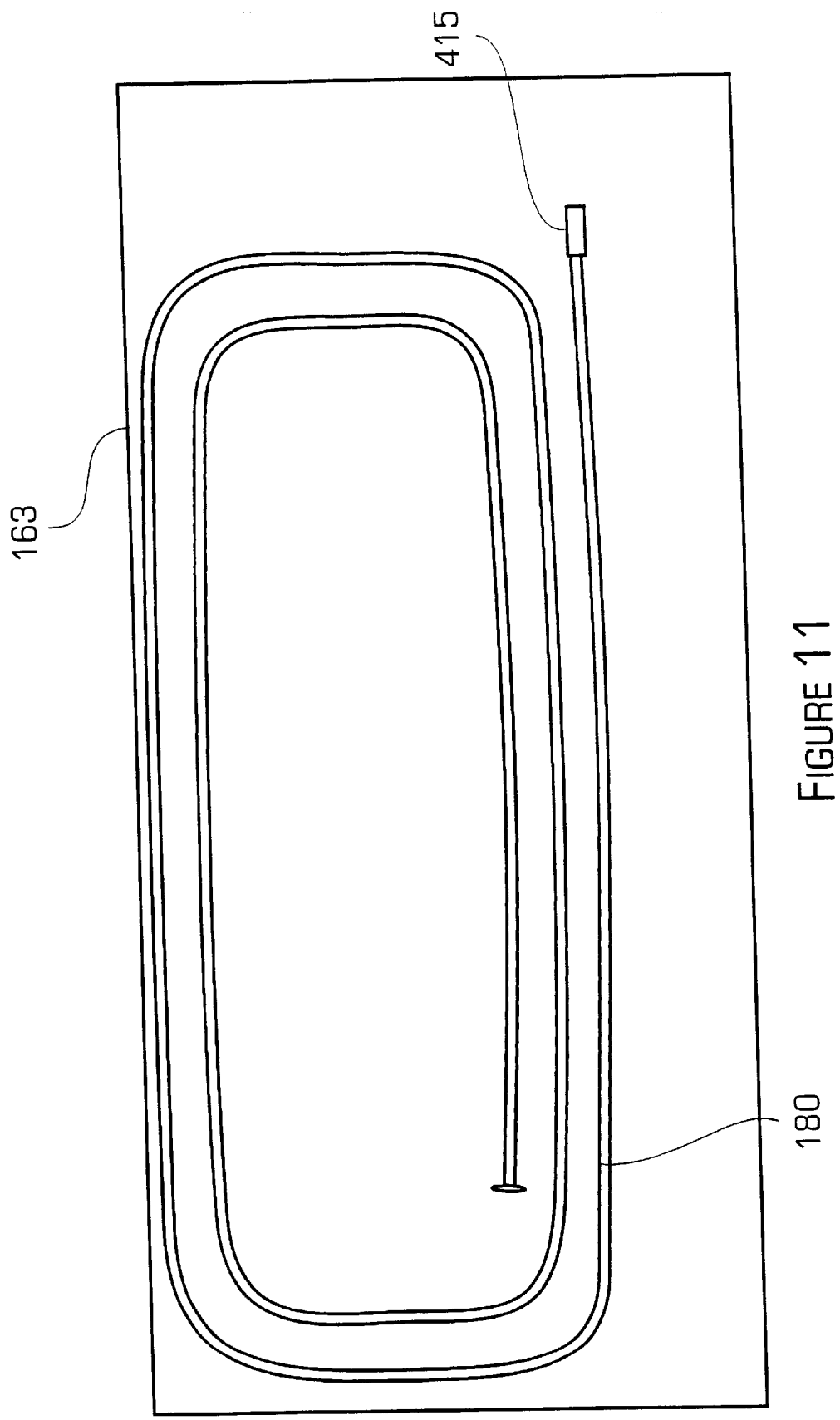
FIG. 11 shows another embodiment of the radiation source cassette comprising a tube in an oval race track design.
Figure 12:
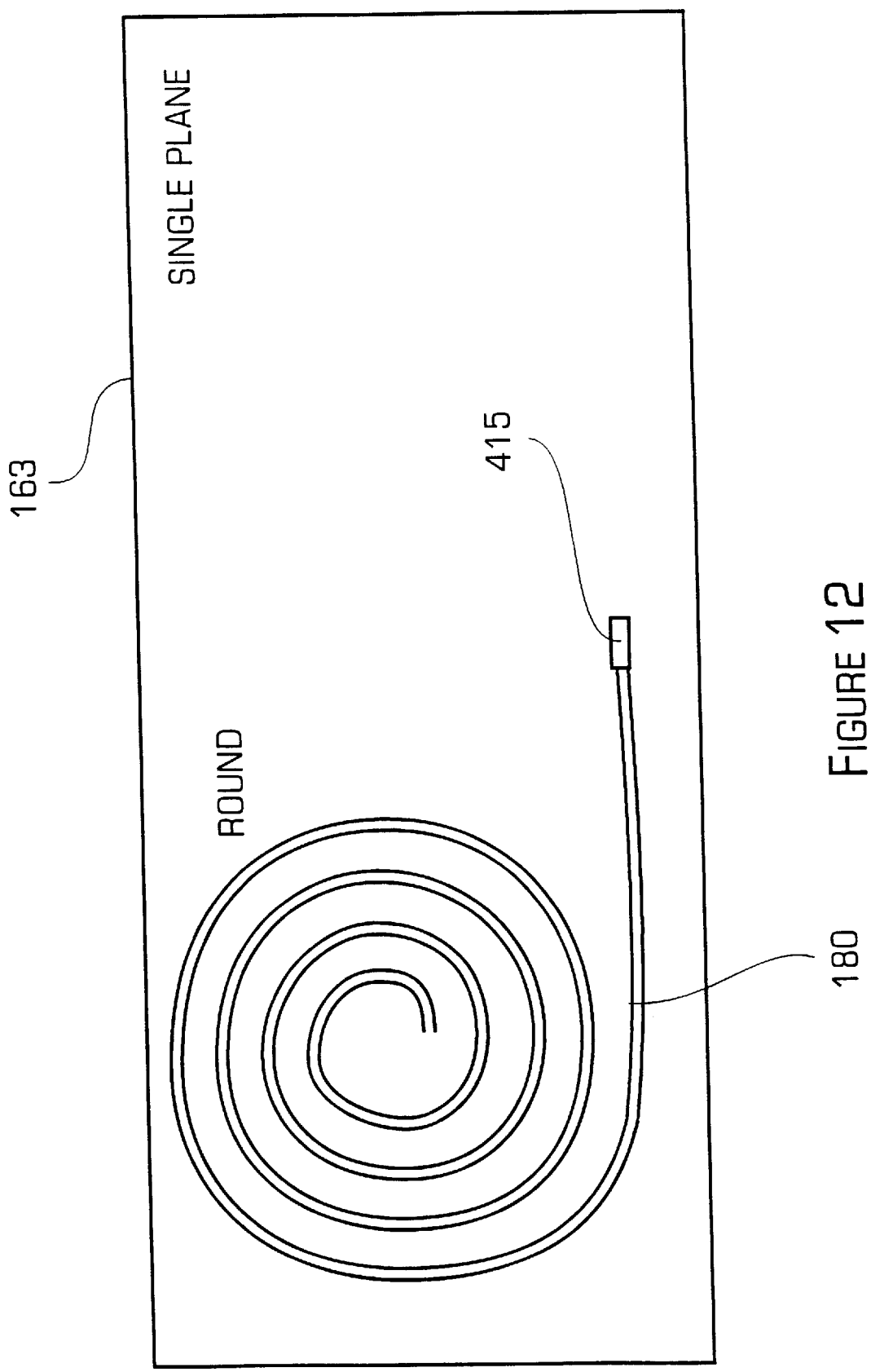
FIG. 12 shows another embodiment of the radiation source cassette comprising a tube in a coiled design.

FIG. 10 shows another embodiment of the radiation source cassette 163. This embodiment of the radiation source cassette 163 includes a first tube 1005, a second tube 1010, multiple rollers 305, and a Y-shaped track. In this embodiment, the radiation source wire 180 is captured inside of the first tube 1005 and the dummy source wire 410 is captured inside of the second tube 1010. The first tube 1005 both stores and helps to guide the radiation source wire 180 through the guide rollers 305 and the motors 167. The guide rollers 305 help to guide the radiation source 415 and the motors 167 drive the radiation source wire 180 through the Y-shaped track as it is delivered to and retracted during radiation treatment. The second tube 1010 both stores and helps to guide the dummy source wire 410 through the guide rollers 305 and the motors 167. The guide rollers 305 help to guide the dummy source 420 and the motors 167 drive the dummy source wire 410 through the Y-shaped track as it is delivered to and retracted from the catheters located in the patient's tumor. The first tube 1005 or the second tube 1010 design can have a variety of different shapes including a single plane oval race track design as shown in FIG. 11, a single plane coiled design as shown in FIG. 12, or a multiple plane spiral design (not shown).

Figure 13:
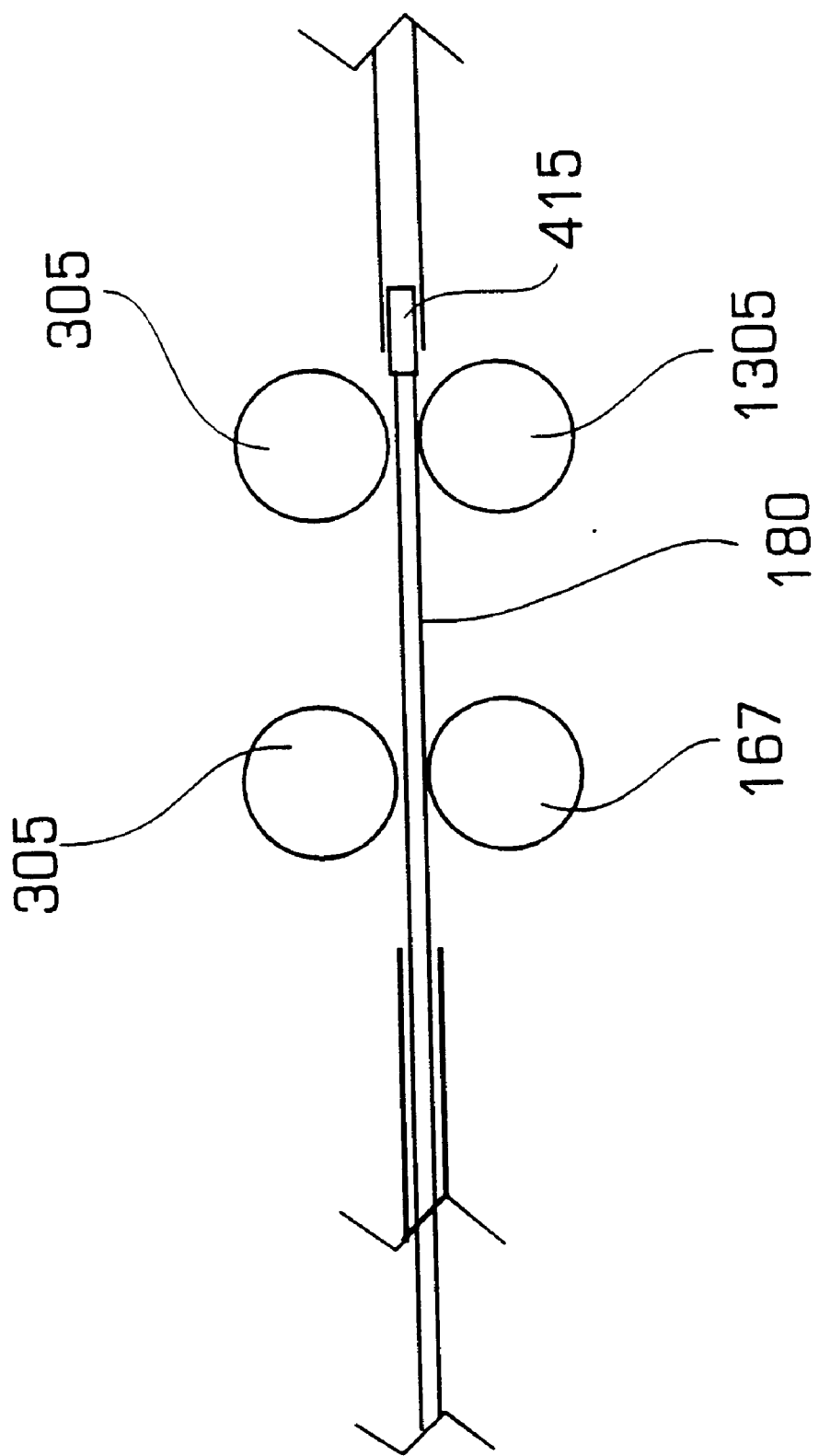
FIG. 13 shows one embodiment of the guide rollers and the motors of the motorized radiation source cassette.

FIG. 13 shows a close up view of the rollers 305 and the motors 167 used in the various embodiments of the motorized radiation source cassette 163 discussed above in FIGS. 5 and 8. However, in this embodiment, the motorized radiation source cassette 163 has two guide rollers 305 and two different types of motors. The first motor 167 is used to advance and retract the radiation source wire 180 or the dummy source wire 410. The second motor 1305 is used only to measure the length of the radiation source wire 180 or the dummy source wire 410 that has been displaced. The host computer 175 utilizes the diameter of the two motors 167 and 1305 and the speed in which the radiation source wire 180 or dummy source wire 410 is being advanced to determine the distance that the radiation source 415 or the dummy source 420 has traveled. This method is reasonably accurate for measuring the distance the radiation source 415 or the dummy source 420 has traveled since the second motor 1305 has no additional forces acting on it. In another embodiment, an optional back-up motor can be used for only dispensing and retracting the radiation source wire 180 or dummy source wire 410 in case of motor failure. The hand crank 197 shown in FIG. 1 can also be used to manually wind-up the radiation source wires 180 or the dummy source wires 410 if the motor 167 is faulty.

Figure 14:
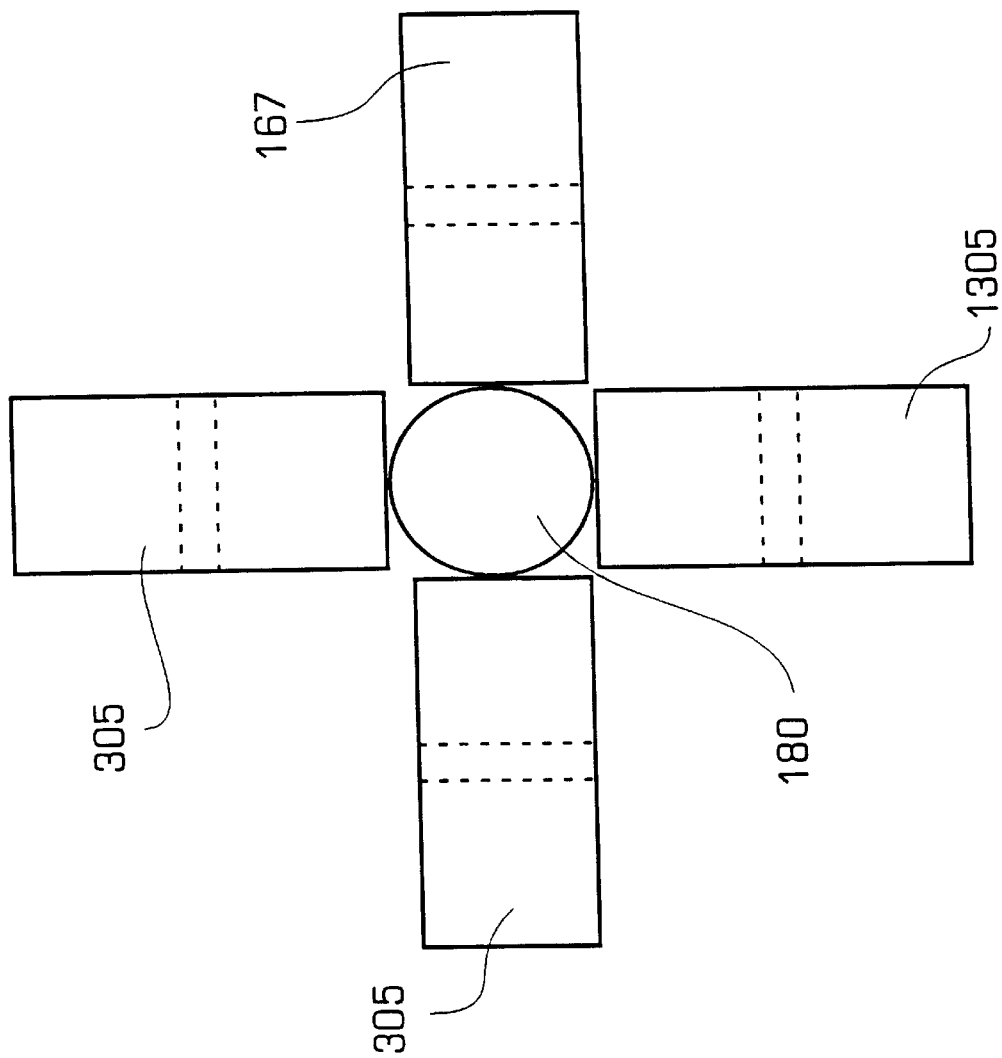
FIG. 14 shows another embodiment of the radiation source cassette where the guide rollers and the motors are stacked on top of each other in perpendicular planes.

In FIG. 13, the two guide rollers 305 are shown above the radiation source wire 180, and the two motors 167 and 1305 are shown below the radiation source wire 180. However, other configurations can have additional roller and motor combinations. The guide rollers 305 and the motors 167 and 1305 can also be stacked on top of each other in perpendicular planes and separated just enough to allow the radiation source wire 180 or dummy source wire 410 to be inserted between them as shown in FIG. 14. The guide rollers 305 help to guide the radiation source wire 180 or the dummy source wire 410 as they are delivered and retracted to and from the catheters located in the patient's tumor.

Figure 15:
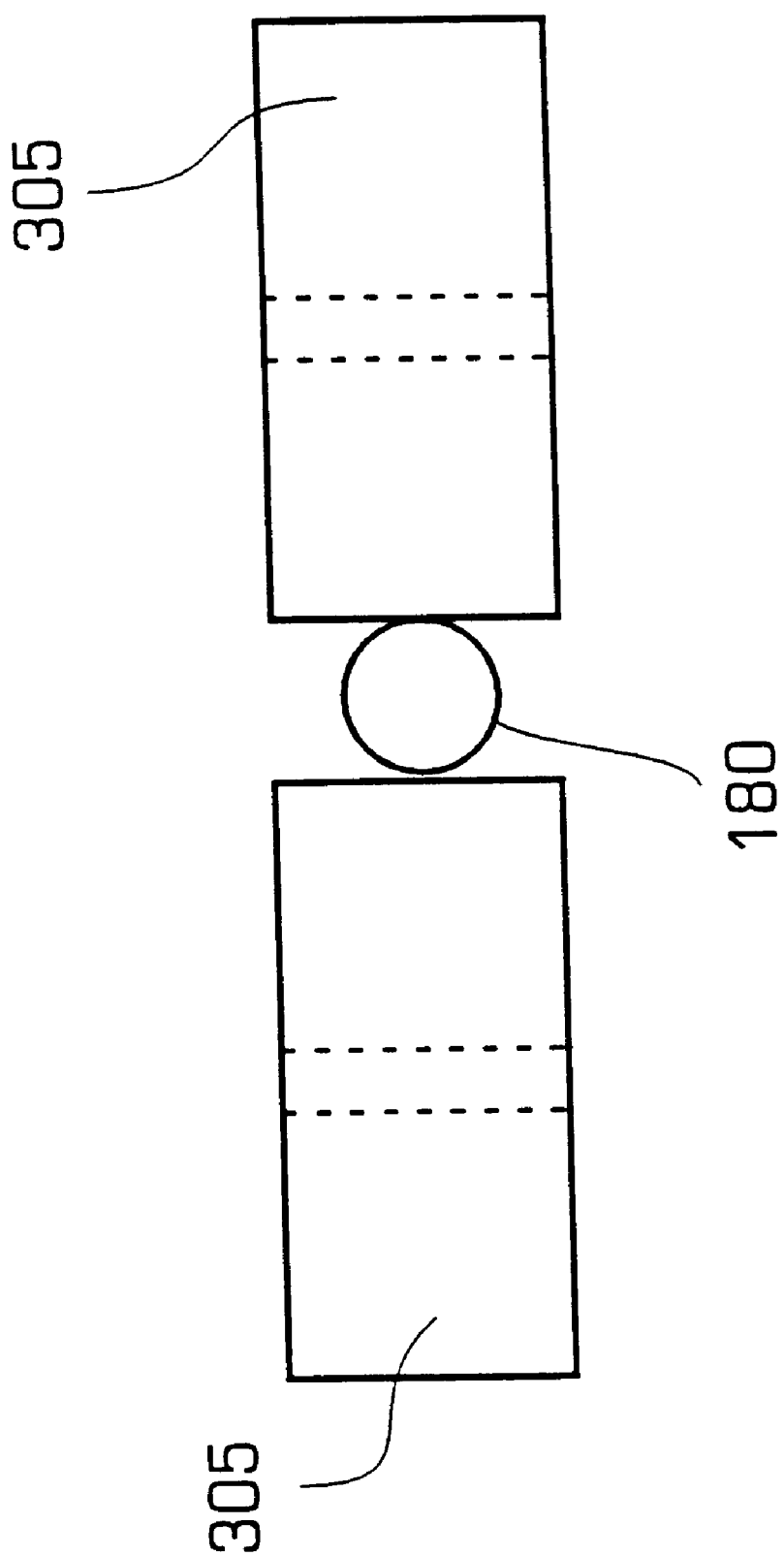
FIG. 15 shows one embodiment of a pair of rollers having a flat contact area.
Figure 16:
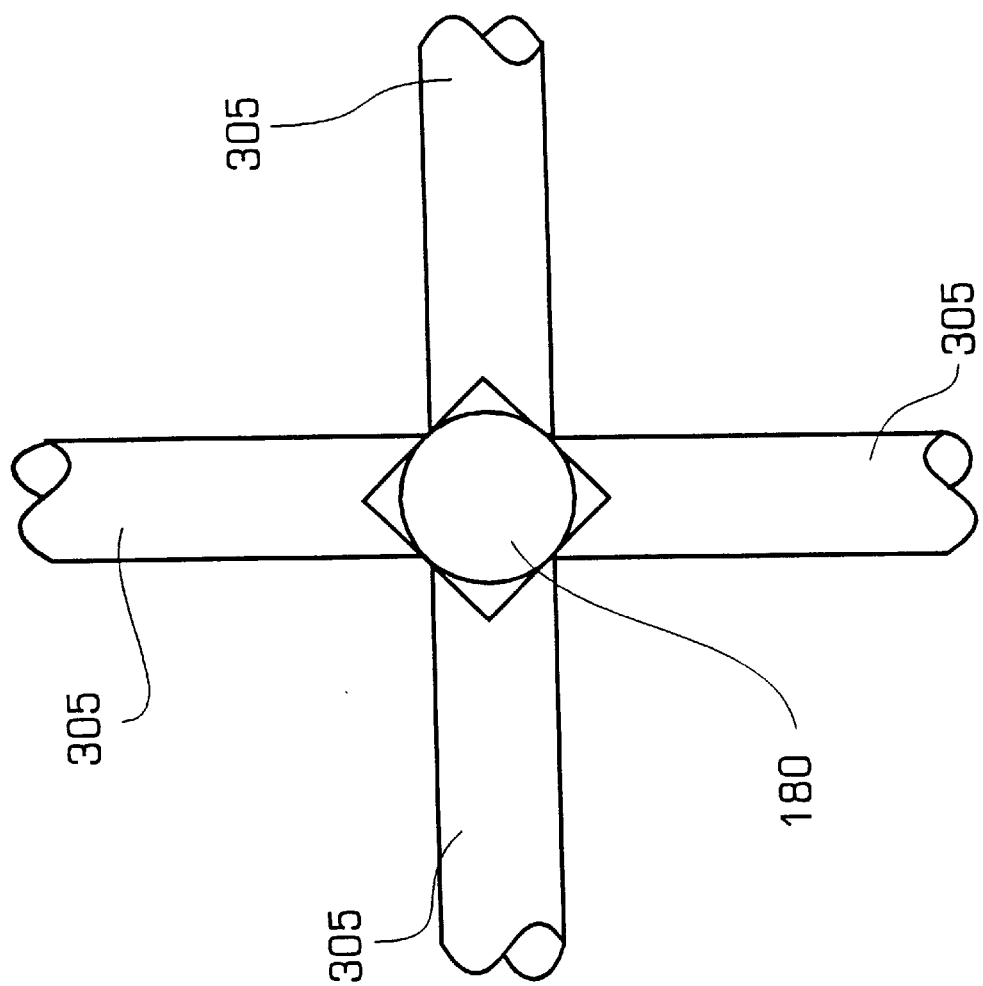
FIG. 16 shows two pairs of rollers where the first pair is stacked horizontally and the second pair is stacked vertically.
Figure 17:
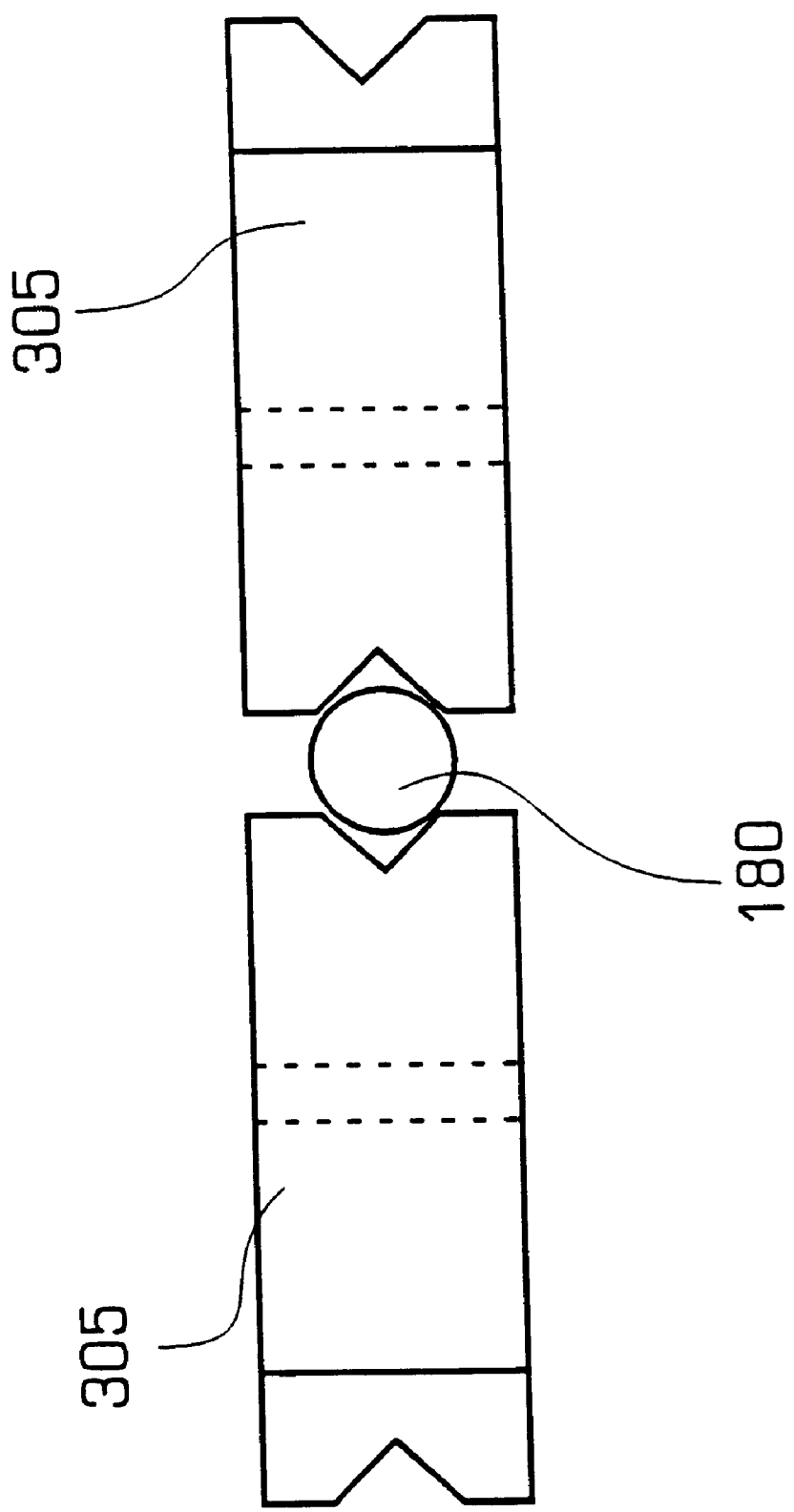
FIG. 17 shows another embodiment of a pair of rollers having a "V" shaped grove at the contact area.
Figure 18:
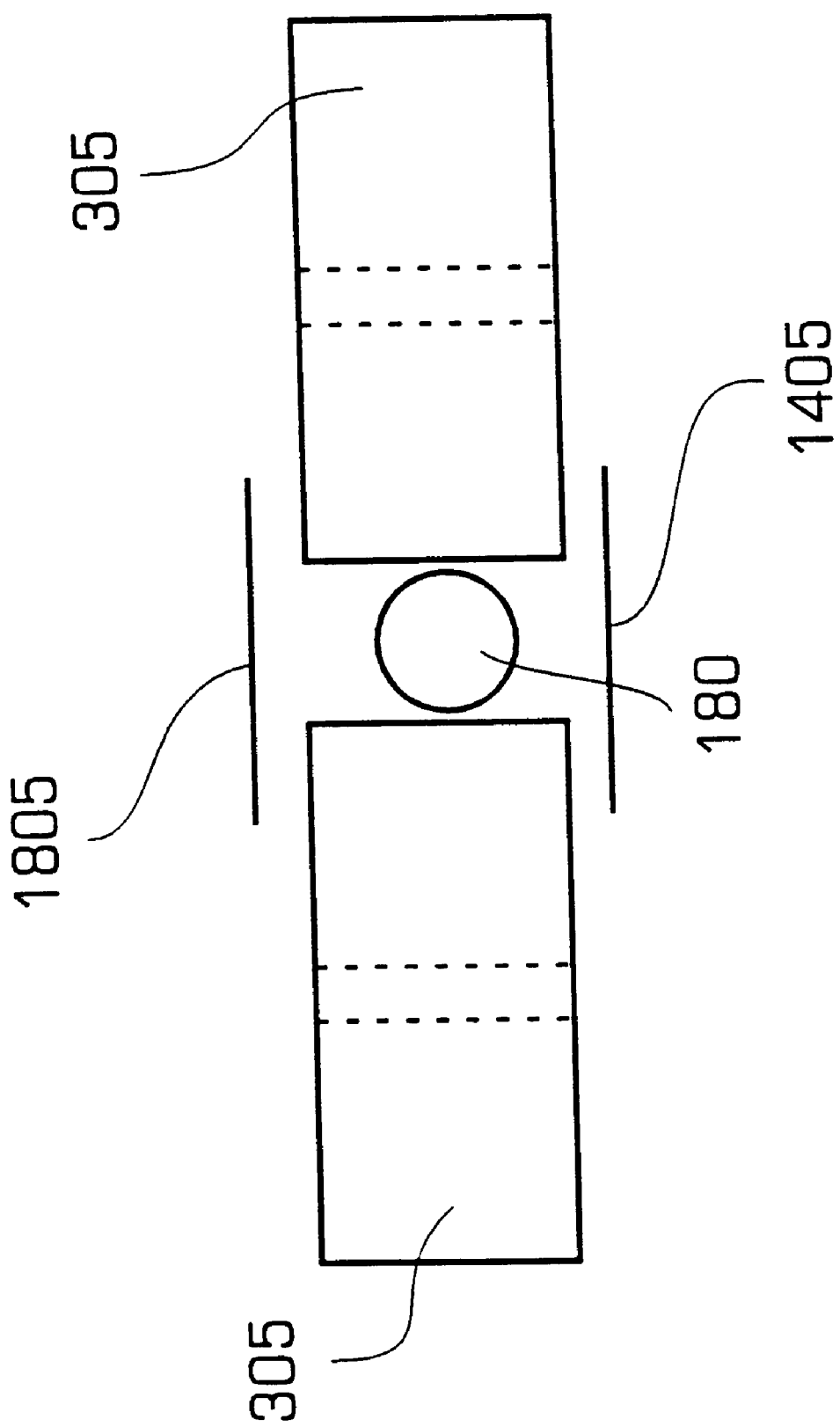
FIG. 18 shows a pair of rollers on either side of the a radiation source wire having a pair of backing plates above and beneath the radiation source wire.

Different embodiments of the guide rollers 305 can have different designs. In one embodiment, the guide rollers 305 can be flat across the section that contacts the radiation source wire 180 or dummy source wire 410 as shown in FIG. 15. In another embodiment, two sets of guide rollers 305 can be used to ensure that the radiation source wire 180 or the dummy source wire 410 is properly contained. One set of guide rollers 305 can be mounted horizontally and the second set of guide rollers 305 can be mounted vertically as shown in FIG. 16. In another embodiment, the guide rollers 305 can have a "V" shaped groove at the end of each guide roller 305 as shown in FIG. 17. The "V" shaped groove better encapsulates the radiation source wire 180 or the dummy source wire 410. In yet another embodiment, in addition to using two sets of guide rollers 305, a pair of backing plates 1805 can be used to help hold the radiation source wire 180 or the dummy source wire 410 as shown in FIG. 18. FIG. 18 shows a pair of rollers 305 on either side of the radiation source wire 180 with a pair of backing plates 1805 above and beneath the radiation source wire 180. In another embodiment (not shown), the guide roller 305 can also contain a motor which would be more compact and save space.

Figure 19:
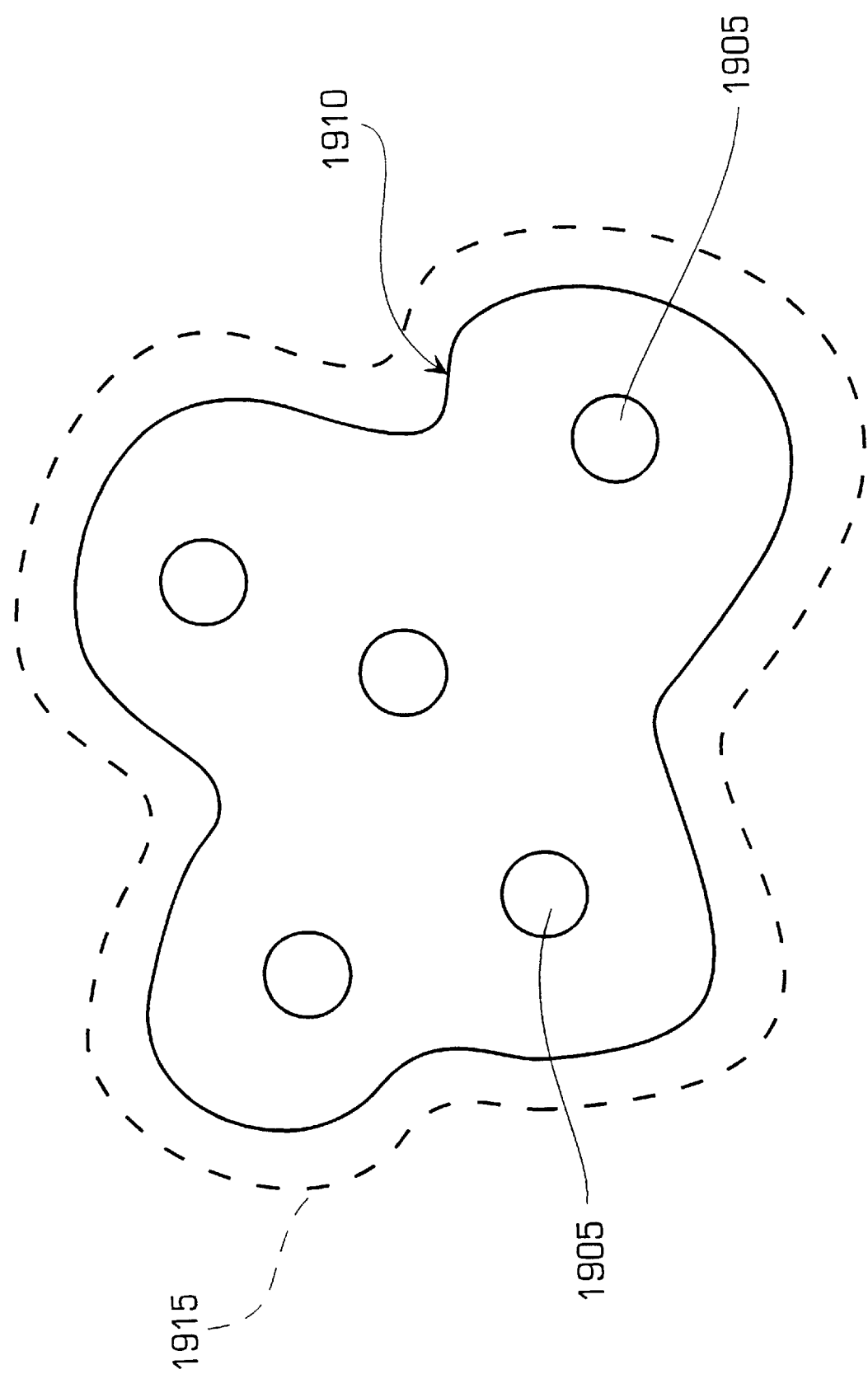
FIG. 19 shows top view of an irregular shaped tumor and treating volume having catheters inserted inside it.

Before one or more radiation sources 415 or dummy sources 420 are delivered to the patient for treatment, the catheters 1905 are inserted into the patient's tumor 1910 as shown in FIG. 19. An example catheter and insertion system is described in copending U.S. application entitled Neutron Brachytherapy Device and Method filed Sep. 13, 1999, Ser. No. 09/395,324 (incorporated by reference herein in its entirety). FIG. 19 shows a top view of an irregular shaped tumor 1910 having an irregular volume. Five catheters 1905 have been inserted into the tumor 1910. The dotted line surrounding the tumor represents the radiation dose volume 1915. By strategically placing the Five catheters 1905 into the tumor 1910 and simultaneously inserting a radiation source 415 or dummy source 420 into each of the five catheters 1905, the treatment time can be significantly reduced. Prior art afteroaders are only able to advance and retract one radiation source 415 at a time. Previous clinical trials using larger Cf-252 sources which were less intense required treatment times anywhere from thirty (30) to sixty (60) hours. This remote afterloader 105 coupled with more highly concentrated sources (Cf-252) are can bring the treatment times down to under five hours, and more typically in the range of one to three hours.

Figure 20:
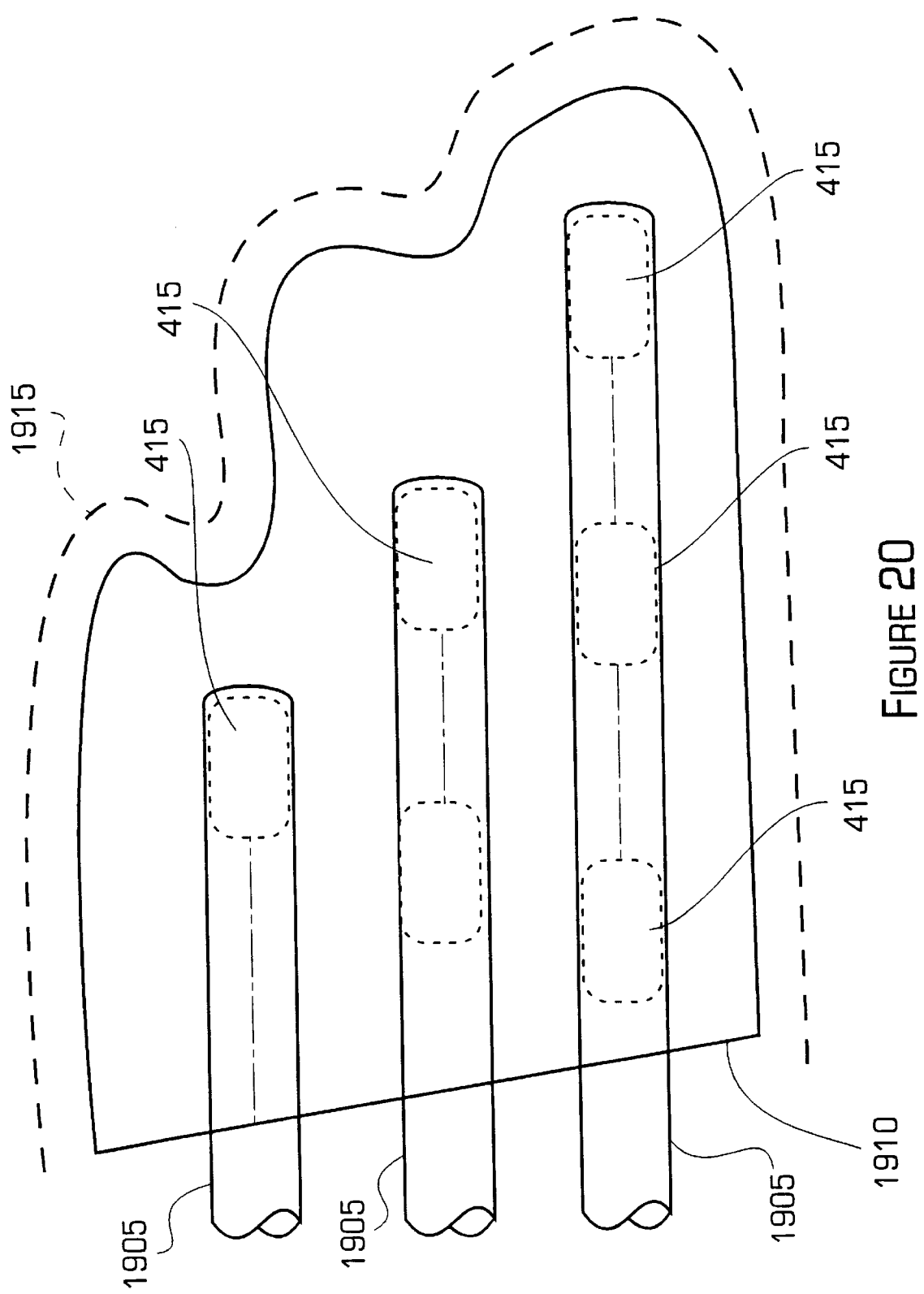
FIG. 20 shows a side view of the irregular shaped tumor having catheters inserted inside of it.

FIG. 20 shows a side view of the tumor 1910 with three catheters 1905 inserted at strategic locations with the tumor 1910. To treat the patient's tumor, the motor 167 pulls the radiation source wire 180 from the reel 310 or tube 1005 and advances the radiation source 415 until it is placed at the far end of the catheter 1905. The radiation source 415 can be left in a location within the catheter 1905 for a specific dwell time. The radiation source 415 can then be retracted slightly and repositioned to another location within the catheter 1905 for a specific dwell time. The dwell times at each location may vary. This process repeats until the radiation source 415 has adequately delivered the prescribed radiation dose at all locations along the length of the catheter 1905. By moving the radiation source 415 along the length of the catheter 1905, the radiation point source 415 has essentially been turned into a line source. This method eliminates the problem in the prior art of trying to determine the correct amount of radiation source to treat a specific size tumor 1910. The same procedure can be done for the dummy source 420 for testing purposes. By strategically placing the catheters 1905 into the tumor 1910 and treating specific locations within the tumor 1910, the entire volume of the tumor 1910 can be treated with radiation while minimizing radiation to surrounding tissue cells.

Figure 21:
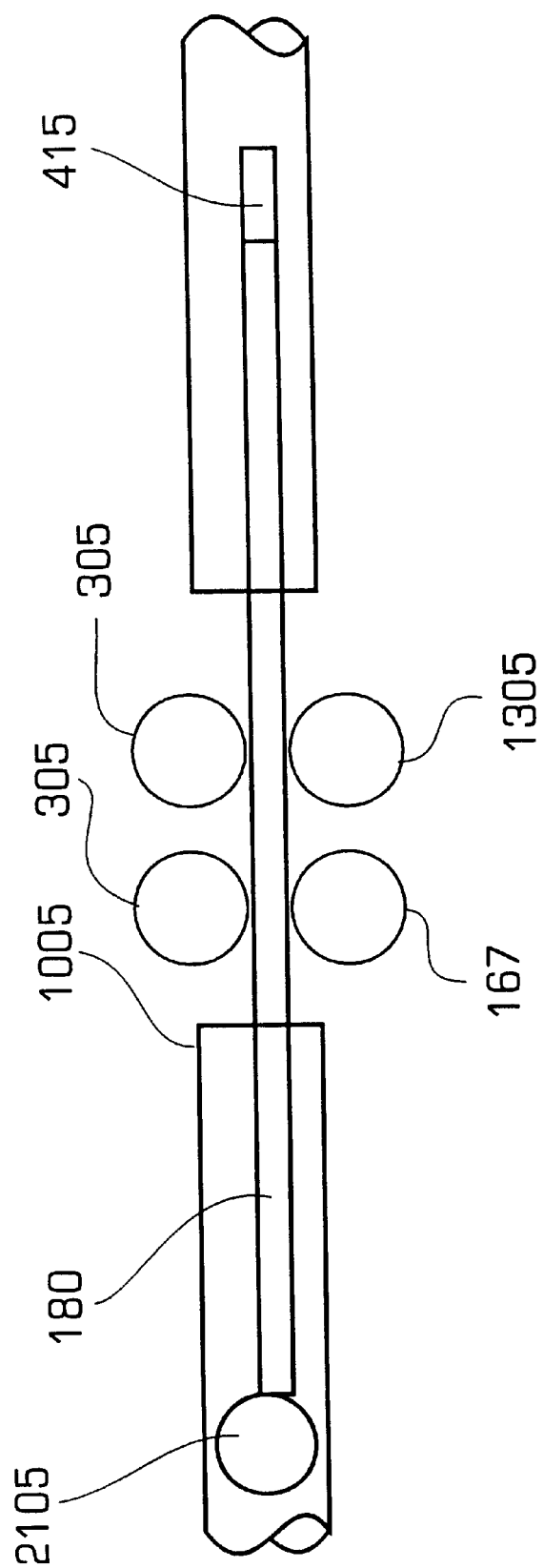
FIG. 21 shows one embodiment of a tube design where the radiation source wire contains a ball at the non-treating end to prevent it from advancing further than a certain length.

If the radiation source wire 180 or the dummy source wire 410 is coiled on a reel, it must be sufficiently long enough to travel the full length of the catheter 1905 positioned inside the tumor 1910, the length inside of the remote afterloader 105 including the storage vault region, plus the distance between the vault and extra length required by the motor region and coiling on the reel 310. If the radiation source wire 180 is contained within a tube 1005, a ball 2105 or handle can be attached to the non-treating end of the radiation source wire 180 to prevent it from exiting the tube 1005 as the radiation source 415 is delivered to the patient's tumor 1910 as shown in FIG. 21. Whether the radiation source wire 180 is on a reel 310 or in a tube 1005, the radiation source wire 180 can never be advanced beyond a specific length. Limiting how far the radiation source 415 can be advanced provides a safety feature in the case of a faulty motor 167 instruction.

Referring back to FIG. 1, the host computer 175 is configured to execute the treatment control software program 185 stored in memory 155. Before the remote afterloader 105 is activated, the doctor first inserts the catheters 1905 either directly into the tumor 1910 volume or into an applicator that has been inserted into the area. An applicator is a plastic shaped form having holes to both hold and space the catheters 1905 apart. Each one of the catheters 1905 are tagged with a number so that they may be distinguished. After the catheters 1905 are all in place and connected to the remote afterloader 105, the remote afterloader 105 can be turned on.

When the treatment control software program 185 is first executed, a screen appears where the patient's name and treatment number are input into the host computer 175 if this step has not already been done. The treatment control software program 185 then accesses the patient's information from the database 160. Included in the patient's information is the prescribed amount of radiation dosing for the patient's tumor. This is very important since each catheter 1905 is placed in a different location within the tumor 1910 and may have different number of dwell positions. Next, the treatment control software program 185 verifies that all radiation sources 415 and dummy sources 420 are in their home positions within the remote afterloader 105 and confirms that the number of catheters 1905 connected match the actual number of catheters 1905 connected to the patient's tumor 1910. If the number does not match, a notice appears on the computer screen 135 to notify the attendant.

Before advancing the radiation sources 415 to the patient's tumor, the treatment control software program 185 first advances the dummy sources 420 to the end of each catheter 1905 to ensure that the radiation sources 415 can be inserted to the furthest location without any kinks. Inserting the dummy source 420 into each catheter 1905 also verifies the distance to the end of each catheter 1905. If any problems occur during the testing with the dummy sources 420 an audible alarm sounds. If the problem can be corrected then treatment can continue. If the problems cannot be corrected, then the treatment is aborted.

As stated before, each catheter 1905 may have a different number of dwell positions depending on where the catheter 1905 has been placed in the patient's tumor. Thus, the treatment control software program 185 independently controls each radiation source wire 180 as they are used during treatment. The treatment control software program 185 tracks and records the time that each radiation source 415 spends in a specific dwell position in the database 160 to assure that the right dosage is applied. Thus, the treatment control software program 185 provides accurate radiation dosimetry for treating the volume of a specific patient's tumor and minimizes the dose delivered to nearby surrounding healthy tissue or organs.

The speed and feed rates used for delivering and retracting the radiation source wires 180 and dummy source wires 410 can be standardized so that they are not permitted to be modified by an end user, or they can be programmable within the treatment control software program 185. However, the dwell time and incremental dwell lengths should be adjustable and programmable by the user since this varies with each patient. The precise length and adjustments to the dwell time and incremental dwell lengths can be made via a closed-loop system recognizing the number of encoder steps seen by an indexer. When the motor 167 is rotating, the indexer repeatedly compares the number of encoder steps coming in against the number of motor steps being sent out. If the encoder position deviates excessively from the desired position in the course of a move, the indexer assumes the motor has stalled. A correction could be performed to correct this condition. In another embodiment, the encoders can be replaced with rugged motor-mounted resolvers. A resolver is a rugged electromagnetic feedback device that acts like a rotating transformer to provide an analog signal with velocity and position information. Resolvers will work better in an industrial working environment where encoders tend to fail under extreme conditions such as high temperature, vacuum, radiation, or shock and vibration.

The treatment control software program 185 is also executable, for example, to display the direction and movement of the radiation source wires 180 and dummy source wires 410 as they are advanced and retracted from the remote afterloader 105 and count the number of times each radiation source 415 is used to treat a patient. The treatment control software program 185 is also executable to monitor the doors of the treatment room and retract the radiation sources 415 to their home position in the remote afterloader 105 in the case someone enters the treatment room while the radiation sources 415 are in use and track the location of the source wires 180 and dummy wires.

During treatment, if the host system 115 verifies that a source wire 180 or dummy wire is not where it should be, then a warning light illuminates on the display panel. A pressure sensor (not shown) also measures the amount of force being applied to advance the source wires 180 or dummy wires. If the force applied to advance the source wire 180 or dummy wires surpasses the maximum amount allowed by the pressure sensor, an alarm sounds and the source wire 180 or dummy wire are retracted into the remote afterloader 105. If the problem can be corrected, the treatment continues. If not, the treatment is aborted and attempted later after the problem is corrected. Once the treatment control software program 185 has advanced all the radiation source wires 180 to the catheters and completed the treatment, the treatment software program 185 then a retracts them back into the remote afterloader 105. The treatment software control program 185 verifies that all the radiation sources or dummy sources have been retracted into the remote afterloader 105 and a final report is generated.

In summary, the remote afterloader for moving a radiation source into and out of a catheter inserted in a tumor may include one or more radiation source cassettes, one or more motors, and a shielded container for storing the radiation source cassettes and the motor. Each radiation source cassette may include a radiation source wire having the radiation source connected to a treating end and a dummy source wire having a dummy source connected to a treating end. The motor advances and retracts the radiation source wire and the dummy source wire into and out of each radiation source cassette one at a time.

Although the present invention has been described in detail, it should be understood that various changes, substitutions and alterations can be made hereto without departing from the spirit and scope of the invention as described by the appended claims.

What is claimed is:

1. A remote controlled afterloader for moving a high intensity neutron radiation source into and out of a catheter inserted in a tumor, comprising:

a radiation source cassette having a radiation source wire;

the radiation source connected to a treating end of the radiation source wire;

a device for advancing and retracting the radiation source wire into and out of the radiation source cassette;

a shielded storage container for storing the radiation source cassette; and wherein the shielded storage container has sufficient shielding to prevent the escape of neutron source radiation from the high intensity neutron source.

2. The remote controlled afterloader of claim 1, further comprising a radiation source cassette storage unit having multiple slots for storing multiple radiation source cassettes.

3. The remote controlled afterloader of claim 2, wherein the radiation source cassette further comprises:

a dummy source wire;

a dummy source connected to a treating end of the dummy source wire;

a first reel having the radiation source wire coiled around it;

a second reel having the dummy source wire coiled around it;

a Y-shaped track for allowing either the radiation source wire and radiation source or the dummy source wire and dummy source to be advanced and retracted into and out of the radiation source cassette one at a time;

a first set of rollers for receiving the radiation source wire from the first reel and guiding the radiation source wire and radiation source into and out of the Y-shaped track; and a second set of rollers for receiving the dummy source wire from the second reel and guiding the dummy source wire and dummy source into and out of the Y-shaped track.

4. The remote controlled afterloader of claim 3, wherein the first reel and the second reel are positioned vertically within the radiation source cassette such that one is above the other.

5. The remote controlled afterloader of claim 3, wherein the first reel and the second reel are positioned horizontally within the radiation source cassette such that they are located side by side.

6. The remote controlled afterloader of claim 3, wherein the radiation source cassette is motorized and further comprises:
- a first motor for advancing the radiation source wire and the radiation source into and out of the radiation source cassette;
- the first set of rollers configured such that the radiation source wire coiled around the first reel is inserted between the first motor and the first set of rollers, the first set of rollers guiding the radiation source wire and the radiation source into and out of the Y-shaped track;
- a second motor for advancing the dummy source wire and the radiation source into and out of the radiation source cassette; and
- the second set of rollers configured such that the dummy source wire coiled around the second reel is inserted between the second motor and the second set of rollers, the second set of rollers guiding the dummy source wire and the dummy source into and out of the Y-shaped track.

7. The remote controlled afterloader of claim 6, wherein the first and second set of rollers have a "V" shaped groove at the end that touch the radiation source wire and the dummy source wire to better encapsulate and guide the radiation source wire or the dummy source wire, and wherein the first and second set of rollers each comprise backing plates above and beneath the radiation source wire and the dummy source wire to better encapsulate and guide the radiation source wire or the dummy source wire.

8. The remote controlled afterloader of claim 6, wherein the first and second set of rollers have flat cross-sections that contact the radiation source wire.

9. The remote controlled afterloader of claim 1, further comprising a fifth motor for measuring the length of the radiation source wire that has been displaced and a sixth motor for measuring the length of the dummy source wire which has been displaced.

10. The remote controlled afterloader of claim 9, wherein the first set of rollers are on top of the first and fifth motors in a perpendicular plane and separated to allow the radiation source wire to be inserted between the first set of rollers and the first and fifth motors, and wherein the second set of rollers are on top of the second and sixth motors in a perpendicular plane and separated to allow the dummy source wire to be inserted between the first set of rollers and the second and sixth motors.

11. The remote controlled afterloader of claim 6, wherein the first reel comprises a first bearing and the second reel comprises a second bearing.

12. The remote controlled afterloader of claim 6, wherein the first reel further comprises a third motor and the second reel further comprises a fourth motor which advances the radiation source wire and the dummy source wire respectively, into and out of the radiation source cassette.

13. The remote controlled afterloader of claim 6, wherein the first reel and the second reel are positioned vertically within the radiation source cassette such that one is above the other.

14. The remote controlled afterloader of claim 6, wherein the first reel and the second reel are positioned horizontally within the radiation source cassette such that they are located side by side.

15. The remote controlled afterloader of claim 3, wherein the radiation source cassette further comprises a first tube for storing the radiation source wire, and a second tube for storing the dummy source wire.

16. The remote controlled afterloader of claim 15, wherein the first tube and the second tube are positioned vertically within the radiation source cassette such that one is positioned above the other.

17. The remote controlled afterloader of claim 15, wherein the first tube and the second tube are positioned horizontally within the radiation source cassette such that they are positioned side by side.

18. The remote controlled afterloader of claim 15, wherein the first tube and the second tube have an oval race track design.

19. The remote controlled afterloader of claim 15, wherein the first tube and the second tube have a single plane coiled design.

20. The remote controlled afterloader of claim 15, wherein the first tube and the second tube have a multiple plane spiral design.

21. The remote controlled afterloader of claim 15, wherein a first ball is attached to a non-treating end of the radiation source wire and a second ball is attached to a non-treating end of the dummy source wire to keep the radiation source wire or the dummy source wire from exiting the first tube and second tube respectively.

22. The remote controlled afterloader of claim 1, further comprising a host computer for controlling the remote afterloader, the host computer comprising:
- a memory for storing a software treatment control program;
- a central processing unit electrically connected to the memory for receiving and processing digital information from the remote afterloader and executing the software applications stored in the memory;
- a graphical user interface to display the digital information; and
- a means for inputting data into the host computer.

23. The remote controlled afterloader of claim 22, wherein the software treatment control program is executable by the host computer to:
- access patient information stored in a database;
- verify that all radiation sources and dummy sources are within the radiation source cassettes;
- independently control the movement of the radiation source wire and the dummy source wire into and out of the radiation source cassette;
- track the amount of time that the radiation source spends at a dwell position within the catheter;
- provide accurate radiation dosimetry for the treating volume of a specific patient's tumor; and
- sound an alarm and retract all radiation sources into the remote controlled afterloader if an error occurs.

24. The afterloader of claim 1, wherein the shielded storage container further comprises a metal layer that blocks gamma rays and a hydrogenous material layer that slows down the neutrons emitted from the neutron source.

25. The afterloader of claim 24, wherein the shielded storage container further comprises a metal layered cap that closes. an opening in the shielded storage container so that the shielded storage container is used to store the neutron radiation source in between procedures.

26. The afterloader of claim 24, wherein the metal layer further comprises high atomic number material.

27. The afterloader of claim 26, wherein the high atomic number material comprises one of lead, tungsten and depleted uranium.

28. The afterloader of claim 27, wherein the metal layer further comprises a thickness of at least two inches.

29. The afterloader of claim 24, wherein the hydrogenous layer further comprises one of wax, polyethylene and water extended polyester (WEP) resin.

30. The afterloader of claim 29, wherein the hydrogenous layer further comprises a water extended polyester (WEP) resin and a boron additive wherein the WEP slows down the neutrons emitted from the neutron source and the boron additive captures the neutrons.

31. The afterloader of claim 30, wherein the boron additive further comprises one of boric acid and borax.

32. The afterloader of claim 30, wherein the hydrogenous layer is between twelve and eighteen inches thick.

33. The afterloader of claim 1, further comprising a second radiation source cassette having a second radiation source wire, wherein a second radiation source is connected to a treating end of the second radiation source wire, and a second device for advancing and retracting the second radiation source wire into and out of the second radiation source cassette so that the two high intensity neutron radiation sources may be independently and simultaneously inserted into a tumor.

34. The afterloader of claim 1, wherein the shielded storage container further comprises a two inch metal layer that blocks gamma rays and a hydrogenous material layer of about twelve to eighteen inches that slows down the neutrons emitted from the neutron source.

35. The afterloader of claim 34, wherein the shielded storage container further comprises a metal layered cap that closes an opening in the shielded storage container so that the shielded storage container is used to store the neutron source in between procedures.

36. The afterloader of claim 1, wherein the shielded storage container further comprises a metal layered cap that closes an opening in the shielded storage container so that the shielded storage container is used to store the neutron radiation source in between procedures.

37. A remote controlled afterloader for moving a high intensity neutron radiation source into and out of a catheter inserted in a tumor, comprising:
a radiation source cassette having a radiation source wire and the radiation source connected to a treating end of the radiation source wire;
a shielded storage container for storing the radiation source cassette, the shielded storage container has sufficient shielding to prevent the escape of neutron source radiation from the high intensity neutron source; and
means for moving the radiation source wire into and out of the radiation source cassette.

38. The afterloader of claim 37, wherein the shielded storage container further comprises a metal layer that blocks gamma rays and a hydrogenous material layer that slows down the neutrons emitted from the neutron source.

39. The afterloader of claim 38, wherein the shielded storage container further comprises a metal layered cap that closes an opening in the shielded storage container so that the shielded storage container is used to store the neutron source in between procedures.

40. The afterloader of claim 38, wherein the metal layer further comprises high atomic number material.

41. The afterloader of claim 40, wherein the high atomic number material comprises one of lead, tungsten and depleted uranium.

42. The afterloader of claim 40, wherein the metal layer further comprises a thickness of at least two inches.

43. The afterloader of claim 38, wherein the hydrogenous layer further comprises one of wax, polyethylene and water extended polyester (WEP) resin.

44. The afterloader of claim 43, wherein the hydrogenous layer further comprises a water extended polyester (WEP) resin and a boron additive wherein the WEP slows down the neutrons emitted from the neutron radiation source and the boron additive captures the neutrons.

45. The afterloader of claim 44, wherein the boron additive further comprises one of boric acid and borax.

46. The afterloader of claim 44, wherein the hydrogenous layer is between twelve and eighteen inches thick.

47. The afterloader of claim 37, wherein the shielded storage container further comprises a two inch metal layer that blocks gamma rays and a hydrogenous material layer of about twelve to eighteen inches that slows down the neutrons emitted from the neutron radiation source.

48. The afterloader of claim 47, further comprising a second radiation source cassette having a second radiation source wire, wherein a second radiation source is connected to a treating end of the second radiation source wire, and a second means for advancing and retracting the second radiation source wire into and out of the second radiation source cassette so that the two high intensity neutron radiation sources may be independently and simultaneously inserted into a tumor.

49. A method for moving a radiation source connected to a treating end of a radiation source wire into and out of a catheter inserted in a tumor, comprising the steps of:
storing the radiation source and the radiation source wire in a radiation source cassette;
advancing and retracting the radiation source wire into and out of the radiation source cassette; and
storing the radiation source cassette in a shielded storage container, wherein the shielded storage container has sufficient shielding to prevent the escape of neutron source radiation from the high intensity neutron source.

50. The method of claim 49, wherein the radiation source cassette further advanced and retracted.

51. The method of claim 50, wherein the radiation source cassette further comprises:
a dummy source wire;
a dummy source connected to a treating end of the dummy source wire;
a first reel having the radiation source wire coiled around it;
a second reel having the dummy source wire coiled around it;
a Y-shaped track for allowing either the radiation source wire and the radiation source or the dummy source wire and the dummy source to be advanced and retracted into and out of the radiation source cassette one at a time;
a first set of rollers for receiving the radiation source wire from the first reel and guiding the radiation source wire and the radiation source into and out of the Y-shaped track; and
a second set of rollers for receiving the dummy source wire from the second reel and guiding the dummy source wire and the dummy source into and out of the Y-shaped track.

52. The method of claim 51, wherein the first reel and the second reel are positioned vertically within the radiation source cassette such that one is above the other.

53. The method of claim 51, wherein the first reel and the second reel are positioned horizontally within the radiation source cassette such that they are located side by side.

54. The method of claim 51, wherein the radiation source cassette is motorized and further comprises:
- a first motor for advancing the radiation source wire and the radiation source into and out of the radiation source cassette;
- the first set of rollers configured such that the radiation source wire coiled around the first reel is inserted between the first motor and the first set of rollers, the first set of rollers guiding the radiation source wire and the radiation source into and out of the Y-shaped track;
- a second motor for advancing the dummy source wire and the radiation source into and out of the radiation source cassette; and
- the second set of rollers configured such that the dummy source wire coiled around the second reel is inserted between the second motor and the second set of rollers, the second set of rollers guiding the dummy source wire and the dummy source into and out of the Y-shaped track.

55. The method of claim 54, wherein the first and second set of rollers have a "V" shaped groove at the end that touch the radiation source wire and the dummy source wire to better encapsulate and guide the radiation source wire or the dummy source wire, and wherein the first and second set of rollers each comprise backing plates above and beneath the radiation source wire and the dummy source wire to better encapsulate and guide the radiation source wire or the dummy source wire.

56. The method of claim 54, wherein the first reel comprises a first bearing and the second reel comprises a second bearing.

57. The method of claim 54, wherein the first reel further comprises a third motor and the second reel further comprises a fourth motor which advances the radiation source wire and the dummy source wire respectively, into and out of the radiation source cassette.

58. The method of claim 54, wherein the first reel and the second reel are positioned vertically within the radiation source cassette such that one is above the other.

59. The method of claim 54, wherein the first reel and the second are positioned horizontally within the radiation source cassette such that they are located side by side.

60. The method of claim 57, further comprising a fifth motor for measuring the length of the radiation source wire that has been displaced and a sixth motor for measuring the length of the dummy source wire which has been displaced.

61. The method of claim 54, wherein the first set of rollers are on top of the first and fifth motors in a perpendicular plane and separated to allow the radiation source wire to be inserted between the first set of rollers and the first and fifth motors, and wherein the second set of rollers are on top of the second and sixth motors in a perpendicular plane and separated to allow the dummy source wire to be inserted between the first set of rollers and the second and sixth motors.

62. The method of claim 54, wherein the first and second set of rollers have flat cross-sections that contact the radiation source wire.

63. The method of claim 51, wherein the radiation source cassette further comprises a first tube for storing the radiation source wire and a second tube for storing the dummy source wire.

64. The method of claim 63, wherein a first ball is attached to a non-treating end of the radiation source wire and a second ball is attached to a non-treating end of the dummy source wire to keep the radiation source wire or the dummy source wire from exiting the first tube and second tube respectively.

65. The method of claim 63, wherein the first tube and the second tube are positioned vertically within the radiation source cassette such that one is above the other.

66. The method of claim 63, wherein the first tube and the second tube are positioned horizontally within the radiation source cassette such that they are located side by side.

67. The method of claim 63, wherein first tube and the second tube have an oval race track design.

68. The method of claim 63, wherein first tube and the second tube have a single plane coiled design.

69. The method of claim 63, wherein first tube and the second tube have a multiple plane spiral design.

70. The method of claim 49, wherein a host computer controls the movement of the radiation source wire from the radiation source cassette into the catheter and back into the radiation source cassette, the host computer comprising:
- a memory for storing a software treatment control program;
- a central processing unit electrically connected to the memory for receiving and processing digital information from the remote afterloader and executing the software applications stored in the memory;
- a graphical user interface to display the digital information; and
- a means for inputting data into the host computer.

71. The method of claim 70, wherein the software treatment control program is executable by the host computer to:
- access patient information stored in a database;
- verify that all radiation sources and dummy sources are within the radiation source cassettes;
- independently control the movement of the radiation source wire and the dummy source wire into and out of the radiation source cassette;
- track the amount of time that the radiation source spends at a dwell position within the catheter;
- provide accurate radiation dosimetry for the treating volume of a specific patient's tumor; and
- sound an alarm and retract all radiation sources into the remote controlled afterloader if an error occurs.

\* \* \* \* \*